United States Patent
Xu et al.

(10) Patent No.: US 12,042,276 B2
(45) Date of Patent: Jul. 23, 2024

(54) METHODS, DEVICES, AND SYSTEMS FOR PHYSIOLOGICAL PARAMETER ANALYSIS

(71) Applicant: ABBOTT DIABETES CARE INC., Alameda, CA (US)

(72) Inventors: Yongjin Xu, San Ramon, CA (US); Timothy C. Dunn, San Francisco, CA (US); Gary Hayter, Oakland, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 0 days.

(21) Appl. No.: 17/883,518

(22) Filed: Aug. 8, 2022

(65) Prior Publication Data

US 2023/0024262 A1    Jan. 26, 2023

Related U.S. Application Data

(63) Continuation of application No. 15/901,354, filed on Feb. 21, 2018, now Pat. No. 11,406,293.
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0004* (2013.01); *A61B 5/14503* (2013.01);
(Continued)

(58) Field of Classification Search
None
See application file for complete search history.

(56) References Cited

U.S. PATENT DOCUMENTS 9,938,557 B2   4/2018   Higgins
10,955,423 B2   3/2021   Malka et al.
(Continued)

FOREIGN PATENT DOCUMENTS

WO   WO 2017/106461 A1   6/2017
WO   WO 2017/177192 A1   10/2017

OTHER PUBLICATIONS

U.S. Appl. No. 15/901,354 (U.S. Pat. No. 11,406,293), filed Feb. 21, 2018 (Aug. 9, 2022).
(Continued)

*Primary Examiner* — Michael R Bloch
(74) *Attorney, Agent, or Firm* — Baker Botts L.L.P.

(57) ABSTRACT

Methods, devices, and systems may use a kinetic model to determine physiological parameters related to the kinetics of red blood cell glycation, elimination, and generation. Such physiological parameters can be used, for example, to determine a more reliable calculated HbA1c. In another example, a method may comprise: receiving a plurality of glucose levels over a time period; receiving a glycated hemoglobin (HbA1c) level corresponding to an end of the time period; determining at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of glucose levels and (2) the HbA1c level; and adjusting a glucose level target based on the at least one physiological parameter.

20 Claims, 14 Drawing Sheets

Related U.S. Application Data

(60) Provisional application No. 62/623,134, filed on Jan. 29, 2018, provisional application No. 62/461,739, filed on Feb. 21, 2017.

(51) Int. Cl.
- *A61B 5/1486* (2006.01)
- *A61M 5/172* (2006.01)
- *G01N 33/557* (2006.01)
- *G01N 33/72* (2006.01)
- *G16H 20/17* (2018.01)

(52) U.S. Cl.
CPC .......... *A61B 5/14865* (2013.01); *A61B 5/417* (2013.01); *A61B 5/4836* (2013.01); *A61B 5/4839* (2013.01); *A61B 5/6833* (2013.01); *A61B 5/7221* (2013.01); *A61B 5/7275* (2013.01); *A61B 5/7278* (2013.01); *A61B 5/7282* (2013.01); *A61B 5/742* (2013.01); *A61B 5/746* (2013.01); *A61M 5/1723* (2013.01); *G01N 33/557* (2013.01); *G01N 33/723* (2013.01); *G16H 20/17* (2018.01)

(56) References Cited

U.S. PATENT DOCUMENTS

| | | | | |
|---|---|---|---|---|
| 2008/0201325 | A1* | 8/2008 | Doniger | G06N 20/00 707/999.005 |
| 2008/0319381 | A1* | 12/2008 | Yodfat | A61M 5/1723 604/65 |
| 2009/0043541 | A1* | 2/2009 | Brauker | A61M 5/1723 702/189 |
| 2009/0299151 | A1* | 12/2009 | Taub | A61B 5/14546 600/300 |
| 2009/0299152 | A1 | 12/2009 | Taub et al. | |
| 2010/0168539 | A1 | 7/2010 | Palerm et al. | |
| 2017/0108487 | A1 | 4/2017 | Higgins | |

OTHER PUBLICATIONS

U.S. Appl. No. 15/901,354, filed Jun. 30, 2022 Issue Fee Payment.
U.S. Appl. No. 15/901,354, filed Apr. 1, 2022 Notice of Allowance.
U.S. Appl. No. 15/901,354, filed Feb. 18, 2022 Amendment and Request for Continued Examination (RCE).
U.S. Appl. No. 15/901,354, filed Nov. 18, 2021 Final Office Action.
U.S. Appl. No. 15/901,354, filed Jul. 29, 2021 Response to Non-Final Office Action.
U.S. Appl. No. 15/901,354, filed Mar. 29, 2021 Non-Final Office Action.
U.S. Appl. No. 15/901,354, filed Jan. 26, 2021 Request for Continued Examination (RCE).
U.S. Appl. No. 15/901,354, filed Jan. 19, 2021 Advisory Action.
U.S. Appl. No. 15/901,354, filed Jan. 12, 2021 Amendment and Request for Continued Examination (RCE).
U.S. Appl. No. 15/901,354, filed Jan. 12, 2021 Response after Final Action.
U.S. Appl. No. 15/901,354, filed Nov. 13, 2020 Final Office Action.
U.S. Appl. No. 15/901,354, filed Aug. 3, 2020 Response to Non-Final Office Action.
U.S. Appl. No. 15/901,354, filed Apr. 3, 2020 Non-Final Office Action.
Golkar et al., "Assessment of the relationship between glucose and A1c using kinetic modeling," Journal of Diabetes and its Complications, 20:285-294 (2006).
International Search Report and Written Opinion received in corresponding PCT Application No. PCT/US2018/018960, dated May 3, 2018.
Leow, "Glycated Hemoglobin (HbA1c): Clinical Applications of a Mathematical Concept," ACTA Informatica Medica, 24(4):233 (2016).
Ping et al., "Extremely high (20%) glycated haemoglobin A1c in patents with normal haemoglobin and erythrocyte parameters," Endocrine, 44(2):542-543 (2013).

* cited by examiner

METHODS, DEVICES, AND SYSTEMS FOR PHYSIOLOGICAL PARAMETER ANALYSIS

CROSS-REFERENCE TO RELATED APPLICATIONS

The present application is a continuation of U.S. patent application Ser. No. 15/901,354 filed Feb. 21, 2018, which claims priority to U.S. Provisional Application Nos. 62/623,134 filed Jan. 29, 2018 and 62/461,739 filed Feb. 21, 2017.

STATEMENT REGARDING FEDERALLY SPONSORED RESEARCH OR DEVELOPMENT

Not applicable.

BACKGROUND

The measurement of various analytes within an individual can sometimes be vital for monitoring the condition of their health. During normal circulation of red blood cells in a mammal such as a human body, glucose molecules attach to hemoglobin, which is referred to as glycosylated hemoglobin (also referred to as glycated hemoglobin). The higher the amount of glucose in the blood, the higher the percentage of circulating hemoglobin molecules with glucose molecules attached. The level of glycosylated hemoglobin is increased in the red blood cells of subjects with poorly controlled diabetes mellitus. Since glucose molecules stay attached to hemoglobin for the life of the red blood cells (normally no more than about 120 days), the level of glycosylated hemoglobin reflects an average blood glucose level over that period.

Most of hemoglobin is a type called HbA. When glucose molecules attach to HbA molecules, glycosylated HbA is formed, which is referred to as HbA1. HbA1 has three components: HbA1a, HbA1b, and HbA1c. Because a glucose binds more strongly and to a higher degree to HbA1c than HbA1a and HbA1b, a measure of HbA1c in blood (HbA1c test) is often used as an indication of a subject's average blood glucose level over a 120 day period (the average lifetime of a red blood cell). The HbA1c test is performed by drawing a blood sample from a subject at a medical professional's office, which is then analyzed in a laboratory. The HbA1c test may be used as a screening and diagnostic test for pre-diabetes and diabetes. The HbA1c test may be conducted multiple times over a time period to monitor the health of a subject for diagnosis and/or therapy decisions.

Commercially available in vitro blood glucose test strips and in vivo sensors (and their related devices and systems) provide glucose level measurements with varying degree of measurement frequency. These devices also provide an estimated HbA1c ("eHbA1c") value. While both in vitro and in vivo sensors (and their related devices and systems) are known to be reliable and accurate, when comparisons have been made between HbA1c values and eHbA1c values, a notable discrepancy between the two measurements has been observed. Existing eHbA1c methods and devices, with their reliance on static models, and/or broad assumptions and/or less robust data, are generally considered to be less reliable than HbA1c test results. However, HbA1c determination is inconvenient and uncomfortable for subjects, who must periodically have blood drawn for HbA1c tests and then wait for the results. Additionally, subjects and healthcare providers would benefit from a more accurate eHbA1c that would allow both subjects and their health care providers to monitor and respond to any changes in eHbA1c. Thus, a need exists for improved eHbA1c methods and devices.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
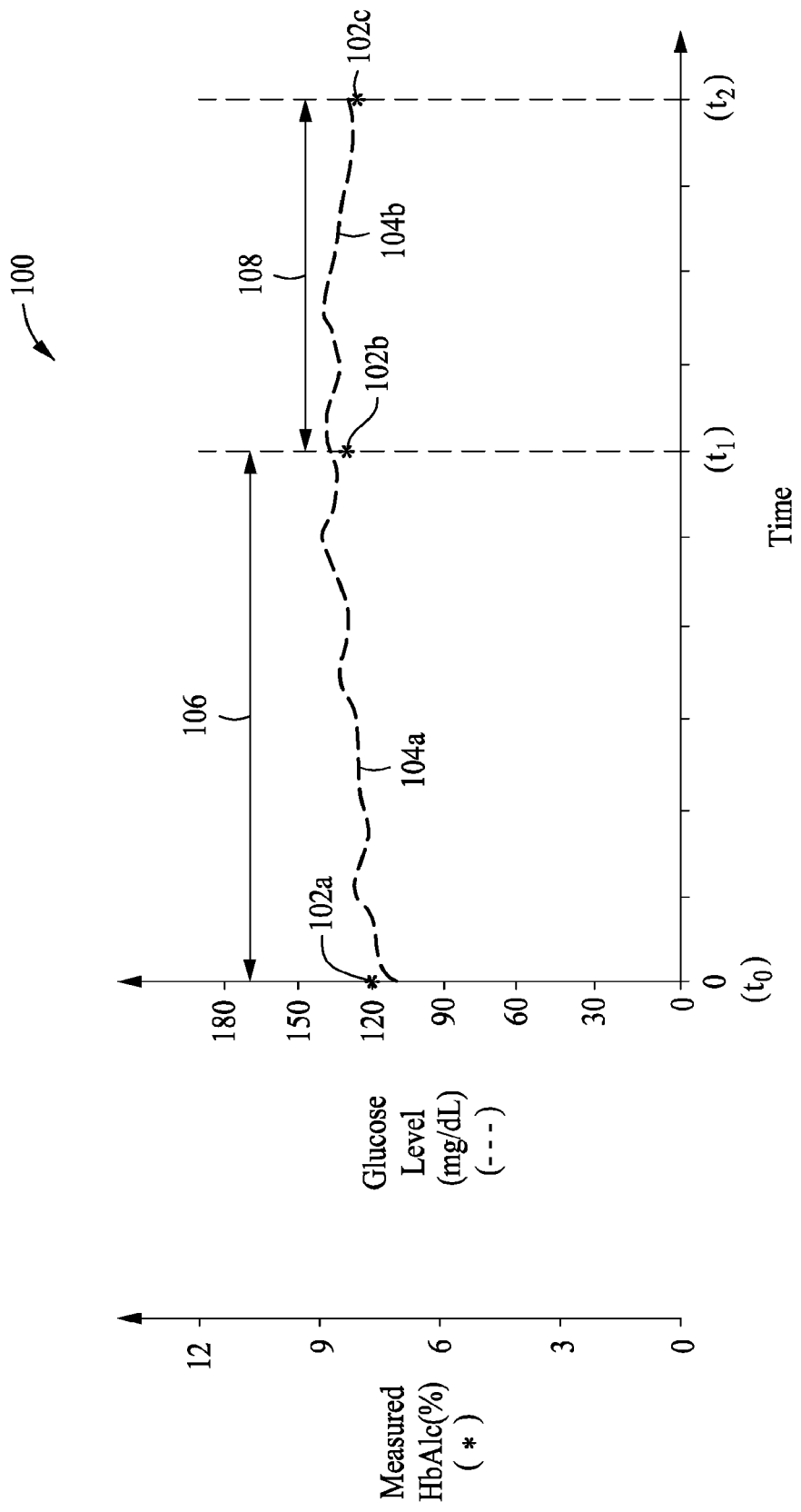
FIG. 1 illustrates an example time line 100 illustrating collection of at least one HbA1c value and a plurality of glucose levels for a time period.

The present disclosure generally describes methods, devices, and systems for determining physiological parameters related to the kinetics of red blood cell glycation, elimination, and generation within the body of a subject. Such physiological parameters can be used, for example, to calculate a more reliable calculated HbA1c and/or a personalized target glucose range, among other things.

Kinetic Model

Formula 1 illustrates the kinetics of red blood cell glycation, elimination, and generation, where "G" is free glucose, "R" is a non-glycated red blood cell, and "GR" is s glycated red blood cell. The rate at which glycated red blood cells (GR) are formed is referred to herein as a red blood cell glycation rate constant ($k_{gly}$ typically having units of $dL*mg^{-1}*day^{-1}$).

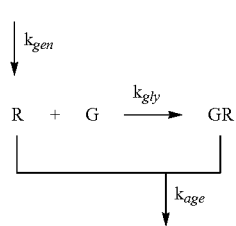

Formula 1

Over time, red blood cells including the glycated red blood cells are continuously eliminated from a subject's circulatory system and new red blood cells are generated, typically at a rate of approximately 2 million cells per second. The rates associated with elimination and generation are referred to herein as a red blood cell elimination constant ($k_{age}$ typically having units of $day^{-1}$) and a red blood cell generation rate constant ($k_{gen}$ typically having units of $M^2/day$), respectively. Since the amount of red blood cells in the body is maintained at a stable level most of time, the ratio of $k_{age}$ and $k_{gen}$ should be an individual constant that is the square of red blood cell concentration.

As described previously, HbA1c is a commonly used analyte indicative of the fraction of the glycated hemoglobin found in red blood cells. Therefore, a kinetic model can be used, for example, to derive a calculated HbA1c based on at least the glucose levels measured for a subject. However, the kinetic model can also be applied to HbA1. For simplicity, HbA1c is uniformly used herein, but HbA1 could be substituted except in instances where specific HbA1c values are used (e.g., see Equations 11 and 12). In such instances, specific HbA1 values could be used to derive similar equations.

Typically, when kinetically modeling physiological processes, assumptions are made to focus on the factors that affect the physiological process the most and simplify some of the math.

The present disclosure uses only the following set of assumptions to kinetically model the physiological process illustrated in Formula 1. First, glucose concentration is high enough not to be affected by the red blood cell glycation reaction. Second, there is an absence of abnormal red blood cells that would affect HbA1c measurement and the hematocrit is constant for the period of interest. This assumption was made to exclude extreme conditions or life events that are not normally present and may adversely affect the accuracy of the model. Third, the glycation process has first order dependencies on both red blood cell and glucose concentrations. Fourth, newly-generated red blood cells have a negligible amount of glycated hemoglobin, based on previous reports that reticulocyte HbA1c is very low and almost undetectable. Fifth, red blood cell production inversely correlates with total cellular concentration, whereas elimination is a first order process.

With the five assumptions described above for this kinetic model, the rate of change in glycated and non-glycated red blood cell can be modeled by differential Equations 1 and 2.

$$d[GR]/dt = k_{gly}[G][R] - k_{age}[GR] \quad \text{Equation 1}$$

$$(d[R])/dt = k_{gen}/C - k_{age}[R] - k_{gly}[G][R] \quad \text{Equation 2}$$

where $C = [R] + [GR]$ (Equation 2a), or the whole population of red blood cells where C typically has units of M (molar), where [R] and [GR] typically have units of M, and where [G] typically has units of mg/dL.

Assuming a steady state, where the glucose level is constant and the glycated and non-glycated red blood cell concentrations remain stable ($d[GR]/dt = (d[R])/dt = 0$), the following two equations can be derived. Equation 3 defines the apparent glycation constant K (typically with units of dL/mg) as the ratio of $k_{gly}$ and $k_{age}$, whereas Equation 4 establishes the dependency between red blood cell generation and elimination rates.

$$K = k_{gly}/k_{age} = [GR]/[G][R] \quad \text{Equation 3}$$

$$k_{gen}/k_{age} = C^2 \quad \text{Equation 4}$$

For simplicity, $k_{age}$ is used hereafter to describe the methods, devices, and systems of the present disclosure. Unless otherwise specified, $k_{gen}$ can be substituted for $k_{age}$. To substitute $k_{gen}$ for $k_{age}$, Equation 4 would be rearranged to $k_{gen} = k_{age} * C^2$.

HbA1c is the fraction of glycated hemoglobin as shown in Equation 5.

$$HbA1c = [GR]/C = (C - [R])/C \quad \text{Equation 5}$$

In a hypothetical state when a person infinitely holds the same glucose level, HbA1c in Equation 5 can be defined as "equilibrium HbA1c" (EA) (typically reported as a % (e.g., 6.5%) but used in decimal form (e.g., 0.065) in the calculations). For a given glucose level, EA (Equation 6) can be derived from Equations 2a, 3, and 5.

$$EA = (k_{gly}[G])/(k_{age} + k_{gly}[G]) = [G]/(K^{-1} + [G]) \quad \text{Equation 6}$$

EA is an estimate of HbA1c based on a constant glucose concentration [G] for a long period. This relationship effectively approximates the average glucose and HbA1c for an individual having a stable day-to-day glucose profile. EA depends on K, the value of which is characteristic to each subject. Equation 6 indicates that the steady glucose is not linearly correlated with EA. Steady glucose and EA may be approximated with a linear function within a specific range of glucose level, but not across the full typical clinical range of HbA1c. Furthermore, in real life with continuous fluctuations of glucose levels, there is no reliable linear relationship between laboratory HbA1c and average glucose for an individual.

Others have concluded this also and produced kinetic models to correlate a measured HbA1c value to average glucose levels. For example, The American Diabetes Association has an online calculator for converting HbA1c values to estimated average glucose levels. However, this model is based on an assumption that $k_{age}$ and $k_{gly}$ does not substantially vary between subjects, which is illustrated to be false in Example 1 below. Therefore, the model currently adopted by the American Diabetes Association considers $k_{age}$ and $k_{gly}$ as constants and not variable by subject.

A more recent model has been developed that removed the assumption that red blood cell life is constant. However, the more recent model still assumes that $k_{gly}$ does not substantially vary between subjects.

In contrast, both $k_{age}$ and $k_{gly}$ are variables for the kinetic models described herein. Further, a subject's $k_{gly}$ is used in some embodiments to derive personalized parameters relating to the subject's diabetic condition and treatment (e.g., a medication dosage, a supplement dosage, an exercise plan, a diet/meal plan, and the like).

Continuing with the kinetic model of the present disclosure, the HbA1c value (HbA1c$_t$) at the end of a time period t (Equation 7) can be derived from Equation 1, given a starting HbA1c (HbA1c$_0$) and assuming a constant glucose level [G] during the time period.

$$HbA1c_t = EA + (HbA1c_0 - EA) * e^{-(k_{gly}[G] + k_{age})t} \quad \text{Equation 7}$$

To accommodate changing glucose levels over time, each individual's glucose history is approximated as a series of time intervals $t_i$ with corresponding average glucose levels [$G_i$]. Applying Equation 7 recursively, HbA1c$_z$ at the end of time interval $t_z$ can be expressed by Equation 8 for numerical calculations.

$$HbA1c_z = EA_z(1-D_z) + \Sigma_{i=1}^{z-1}[EA_i(1-D_i)\Pi_{j=i+1}^{z}D_j] + HbA1c_0\Pi_{j=1}^{z}D_j \quad \text{Equation 8}$$

where the decay term $D_i = e^{-(k_{gly}[G_i] + k_{age})t_i}$ (Equation 8a).

When solving for $k_{age}$ and $k_{gly}$ using Equations 6, 7, or 8, $k_{age}$ and $k_{gly}$ may be bounded to reasonable physiological limits, by way of nonlimiting example, of $5.0*10^{-6}$ dL*mg$^{-1}$*day$^{-1}$ < $k_{gly}$ < $8.0*10^{-6}$ dL*mg$^{-1}$*day$^{-1}$ and $0.006 < k_{age} < 0.024$. Additionally or alternatively, an empirical approach using the Broyden-Fletcher-Goldfarb-Shanno algorithm can be used with estimated initial values for $k_{gly}$ and $k_{age}$ (e.g., $k_{gly} = 4.4*10^{-6}$ dL*mg$^{-1}$*day$^{-1}$ and $k_{age} = 0.0092$ day$^{-1}$). The more glucose level data points and measured HbA1c data points, the more accurate the physiological parameters described herein are.

The value HbA1c$_z$ is the estimated HbA1c of the present kinetic model, which is referred to herein as cHbA1c (calculated HbA1c) to distinguish from other eHbA1c described herein.

As described previous and illustrated in Equation 8, EA$_i$ and D$_i$ are both affected by glucose level [$G_i$], $k_{gly}$, and $k_{age}$. In addition, D$_i$ depends on the length of the time interval $t_i$. Equation 8 is the recursive form of Equation 7. Equations 7 and 8 describe the relationship among HbA1c, glucose level, and individual red blood cell kinetic constants $k_{gly}$ and $k_{age}$.

Unless otherwise specified, the typical units described are associated with their respective values. One skilled in the art would recognize other units and the proper conversions. For example, [G] is typically measured in mg/dL but could be converted to M using the molar mass of glucose. If [G] is used in M or any other variable is used with different units, the equations herein should be adjusted to account for differences in units.

Calculating Physiological Parameters from the Kinetic Model

Embodiments of the present disclosure provide kinetic modeling of red blood cell glycation, elimination, and generation within the body of a subject.

The physiological parameters $k_{gly}$, $k_{age}$, and/or K can be derived from the equations described herein given at least one measured HbA1c value (also referred to as HbA1c level measurement) and a plurality of glucose levels (also referred to as glucose level measurements) over a time period immediately before the HbA1c measurement.

FIG. 1 illustrates an example time line 100 illustrating collection of at least one measured HbA1c value 102a, 102b, 102c and a plurality of glucose levels 104a for a time period 106.

The number of measured HbA1c values 102a, 102b, 102c needed to calculate $k_{gly}$, $k_{age}$, and/or K depends on the frequency and duration of the plurality of glucose levels.

In a first embodiment, one measured HbA1c 102b can be used along with a plurality of glucose measurements over time period 106 to calculate $k_{gly}$, $k_{age}$, and/or K. Such embodiments are applicable to subjects with steady daily glucose measurements for a long time period 106. Then, K may be calculated at time $t_1$ with Equation 6 by replacing EA with the measured HbA1c value 102b and [G] with daily average glucose over time period 106. $k_{gly}$ and $k_{age}$ may be calculated with Equation 8 when the glucose levels are measured for a sufficient amount of time (e.g., over about 200 days) because HbA1c$_0\Pi_{j=1}^{z}D_j$ approaches zero when the time is long. Therefore, an initial HbA1c level measurement is not necessarily required.

Because a first HbA1c value is not measured, the time period 106 of initial glucose level measurements with frequent measurements may be need to be long to obtain an accurate representation of average glucose and reduce error. Using more than 100 days of steady glucose pattern for this method may reduce error. Additional length like 200 days or more or 300 days or more further reduces error.

Embodiments where one measured HbA1c value 102b can be used include a time period 106 about 100 days to about 300 days (or longer) with glucose levels being measured at least about 72 times (e.g., about every 20 minutes) to about 96 times per day (e.g., about every 15 minutes) or more often. Further, in such embodiments, the time between glucose level measurements may be somewhat consistent where an interval between two glucose level measurements should not be more than about an hour. Some missing data glucose measurements are tolerable when using only one measured HbA1c value. Increases in missing data may lead to more error.

Alternatively, in some instances where one measured HbA1c value 102b is used, the time period 106 may be shortened if a subject has an existing glucose level monitoring history with stable, consistent glucose profile. For example, for a subject who has been testing for a prolonged time (e.g., 6 months or longer) but, perhaps, at less frequent or regimented times, the existing glucose level measurements can be used to determine and analyze a glucose profile. Then, if more frequent and regimented glucose monitoring is performed over time period 106 (e.g., about 72 times to about 96 times or more per day over about 14 days or more) followed by measurement of HbA1c 102b, the three in combination may be used to calculate one or more physiological parameters ($k_{gly}$, $k_{age}$, and/or K) at time $t_1$.

Alternatively, in some embodiments, two measured HbA1c values may be used with a first measured HbA1c value 102a at the beginning of a time period 106, a second measured HbA1c value 102b at the end of the time period 106, and a plurality of glucose levels 104a measured during the time period 106. In these embodiments, Equation 8 may be used to calculate one or more physiological parameters ($k_{gly}$, $k_{age}$, and/or K) at time $t_1$. In such embodiments, the plurality of glucose levels 104a may be measured for about 10 days to about 30 days or longer with measurements being, on average, about 4 times daily (e.g., about every 6 hours) to about 24 times daily (e.g., about every 1 hour) or more often.

The foregoing embodiments are not limited to the example glucose level measurement time period and frequency ranges provided. Glucose levels may be measured over a time period of about a few days to about 300 days or more (e.g., about one week or more, about 10 days or more, about 14 days or more, about 30 days or more, about 60 days or more, about 90 days or more, about 120 days or more, and so on). The frequency of such glucose levels may be, on average, about 14,400 times daily (e.g., about every 10 seconds) (or more often) to about 3 times daily (e.g., about every 8 hours) (e.g., 1,440 times daily (e.g., about every minute), about 288 times daily (e.g., about every 5 minutes), about 144 times daily (e.g., about every 10 minutes), about 96 times daily (e.g., about every 15 minutes), about 72 times daily (e.g., about every 20 minutes), about 48 times daily (e.g., about every 30 minutes), about 24 times daily (e.g., about every 1 hour), about 12 times daily (e.g., about every 2 hours), about 8 times daily (e.g., about every 3 hours), about 6 times daily (e.g., about every 4 hours), about 4 times daily (e.g., about every 6 hours), and so on). In some instances, less frequent monitoring (like once or twice daily) may be used where the glucose measurements occur at about the same time (within about 30 minutes) daily to have a more direct comparison of day-to-day glucose levels and reduce error in subsequent analyses.

The foregoing embodiments may further include calculating an error or uncertainty associated with the one or more physiological parameters. In some embodiments, the error may be used to determine if another HbA1c value (not illustrated) should be measured near $t_1$, if one or more glucose levels 104b should be measured (e.g., near $t_1$), if the monitoring and analysis should be extended (e.g., to extend through time period 108 from $t_1$ to $t_2$ including measurement of glucose levels 104b and measurement HbA1c value 102c at time $t_2$), and/or if the frequency of glucose level measurements 104b in an extended time period 108 should be increased relative to the frequency of glucose level measurements 104a during time period 106. In some embodiments, one or more of the foregoing actions may be taken when the error associated with $k_{gly}$, $k_{age}$, and/or K is at or greater than about 15%, preferably at or greater than about 10%, preferably at or greater than about 7%, and preferably at or greater than about 5%. When a subject has an existing disease condition (e.g., cardiovascular disease), a lower error may be preferred to have more stringent monitoring and less error in the analyses described herein.

Alternatively or when the error is acceptable, in some embodiments, one or more physiological parameters ($k_{gly}$, $k_{age}$, and/or K) at time $t_1$ may be used to determine one or more parameters or characteristics for a subject's personalized diabetes management (e.g., a cHbA1c at the end of time period 108, a personalized-target glucose range, and/or a treatment or change in treatment for the subject in the near future), each described in more detail further herein. Optionally, a HbA1c value may be measured at time $t_2$ and the one or more physiological parameters recalculated and applied to a future time period (not illustrated).

The one or more physiological parameter and/or the one or more parameters or characteristics for a subject's personalized diabetes management can be measured and/or calculated for two or more times (e.g., $t_1$ and $t_2$) and compared. For example, $k_{gly}$ at $t_1$ and $t_2$ may be compared. In another example, cHbA1c at $t_2$ and at a future time may be compared. Some embodiments, described further herein, may use such comparisons to (1) monitor progress and/or effectiveness of a subject's personalized diabetes management and, optionally, alter the subject's personalized diabetes management, (2) identify an abnormal or diseased physiological condition, and/or (3) identify subjects taking supplements and/or medicines that effect red blood cell production and/or effect metabolism.

In each of the example methods, devices, and systems utilizing the one or more physiological parameters ($k_{gly}$, $k_{age}$, and K) and related analyses (e.g., personalized-target glucose range, personalized-target average glucose, cHbA1c, and the like). The one or more physiological parameters ($k_{gly}$, $k_{age}$, and K) and related analyses may be updated periodically (e.g., about every 3 months to annually). The frequency of updates may depend on, among other things, the subject's glucose level and diabetes history (e.g., how well the subject stays within the prescribed thresholds), other medical conditions, and the like.

Other Factors

In some of the embodiments described herein that apply the one or more physiological parameters ($k_{gly}$, $k_{age}$, and/or K), one or more other subject-specific parameters may be used in addition to the one or more physiological parameters. Examples of subject-specific parameters may include, but are not limited to, an existing medical condition (e.g., cardiovascular disease, heart valve replacement, cancer, and systemic disorder such as autoimmune disease, hormone disorders, and blood cell disorders), a family history of a medical condition, a current treatment, an age, a race, a gender, a geographic location (e.g., where a subject grew up or where a subject currently lives), a diabetes type, a duration of diabetes diagnosis, and the like, and any combination thereof.

Systems

In some embodiments, determining the one or more physiological parameters ($k_{gly}$, $k_{age}$, and/or K) for a subject may be performed using a physiological parameter analysis system.

Figure 2:
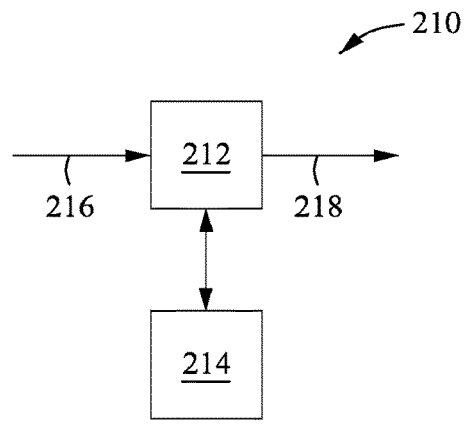
FIG. 2 illustrates an example of a physiological parameter analysis system for providing physiological parameter analysis in accordance with some of the embodiments of the present disclosure.

FIG. 2 illustrates an example of a physiological parameter analysis system 210 for providing physiological parameter analysis in accordance with some of the embodiments of the present disclosure. The physiological parameter analysis system 210 includes one or more processors 212 and one or more machine-readable storage media 214. The one or more machine-readable storage media 214 contains a set of instructions for performing a physiological parameter analysis routine, which are executed by the one or more processors 212.

In some embodiments, the instructions include receiving inputs 216 (e.g., one or more glucose levels, one or more HbA1c levels, one or more physiological parameters ($k_{gly}$, $k_{age}$, and/or K) previously determined, or more other subject-specific parameters, and/or one or more times associated with any of the foregoing), determining outputs 218 (e.g., one or more physiological parameters ($k_{gly}$, $k_{age}$, and/or K), an error associated with the one or more physiological parameters, one or more parameters or characteristics for a subject's personalized diabetes management (e.g., cHbA1c, a personalized-target glucose range, an average-target glucose level, a supplement or medication dosage, among other parameters or characteristics), and the like), and communicating the outputs 218. In some embodiments, communication of the inputs 216 may be via a user-interface (which may be part of a display), a data network, a server/cloud, another device, a computer, or any combination thereof, for example. In some embodiments, communication of the outputs 218 may be to a display (which may be part of a user-interface), a data network, a server/cloud, another device, a computer, or any combination thereof, for example.

A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, and the like). For example, a machine-accessible medium includes recordable/non-recordable media (e.g., read-only memory (ROM), random access memory (RAM), magnetic disk storage media, optical storage media, flash memory devices, and the like).

In some instances, the one or more processors 212 and the one or more machine-readable storage media 214 may be in a single device (e.g., a computer, network device, cellular phone, PDA, an analyte monitor, and the like).

Figure 3:
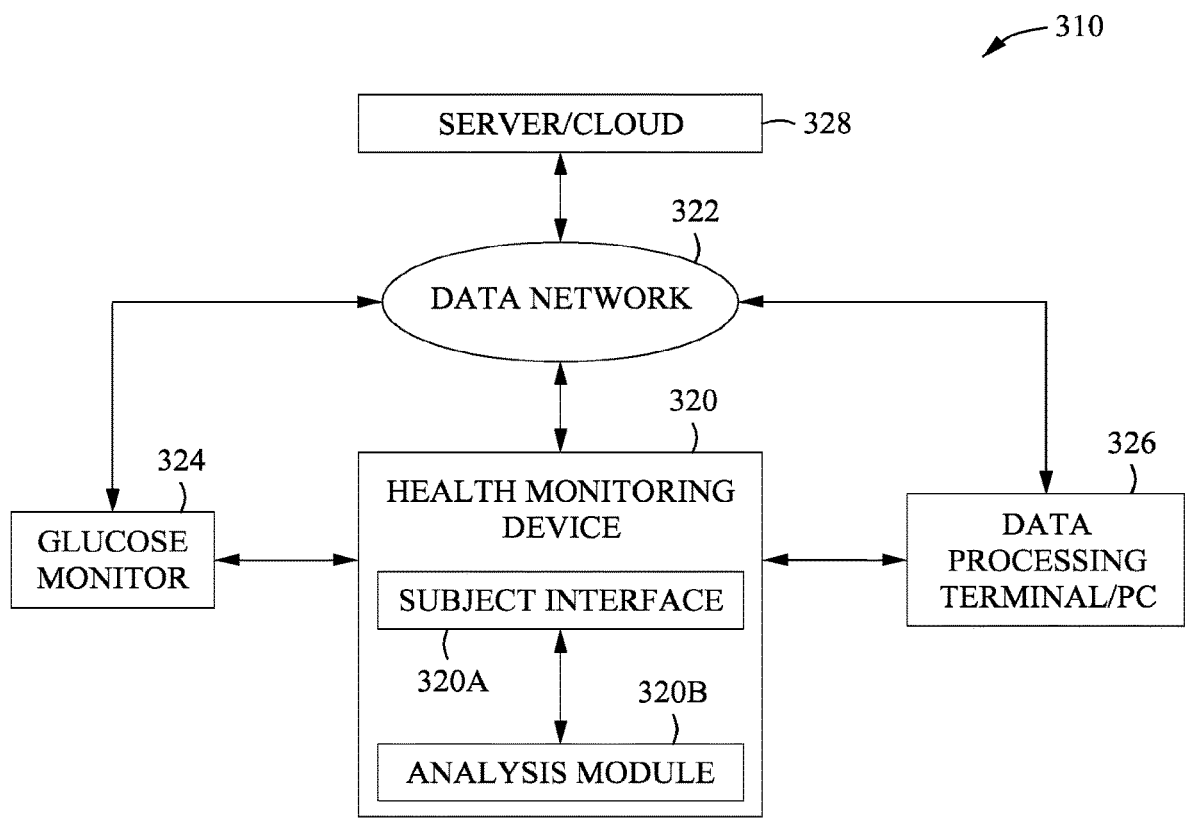
FIG. 3 illustrates an example of a physiological parameter analysis system for providing physiological parameter analysis in accordance with some of the embodiments of the present disclosure.

In some embodiments, a physiological parameter analysis system may include other components. FIG. 3 illustrates another example of a physiological parameter analysis system 310 for providing physiological parameter analysis in accordance with some of the embodiments of the present disclosure.

The physiological parameter analysis system 310 includes health monitoring device 320 with subject interface 320A and analysis module 320B, the health monitoring device 320 is, or may be, operatively coupled to data network 322. Also provided in physiological parameter analysis system 310 is a glucose monitor 324 (e.g., in vivo and/or in vitro (ex vivo) devices or system) and a data processing terminal/personal computer (PC) 326, each operatively coupled to health monitoring device 320 and/or data network 322. Further shown in FIG. 3 is server/cloud 328 operatively coupled to data network 322 for bi-directional data communication with one or more of health monitoring device 320, data processing terminal/PC 326 and glucose monitor 324. Physiological parameter analysis system 310 within the scope of the present disclosure can exclude one or more of server/cloud 328, data processing terminal/PC 326 and/or data network 322.

In certain embodiments, analysis module 320B is programmed or configured to perform physiological parameter analysis and, optionally, other analyses (e.g., cHbA1c, personalized target glucose range, and others described herein). As illustrated, analysis module 320B is a portion of the health monitoring device 320 (e.g., executed by a processor therein). However, the analysis module 320B may alternatively be associated with one or more of server/cloud 328, glucose monitor 324, and/or data processing terminal/PC 326. For example, one or more of server/cloud 328, glucose monitor 324, and/or data processing terminal/PC 326 may comprise machine-readable storage medium (media) with a set of instructions that cause one or more processors to execute the set of instructions corresponding to the analysis module 320B.

While the health monitoring device 320, the data processing terminal/PC 326, and the glucose monitor 324 are illustrated as each operatively coupled to the data network 322 for communication to/from the server/cloud 328, one or more of the health monitoring device 320, the data processing terminal/PC 326, and the glucose monitor 324 can be programmed or configured to directly communicate with the server/cloud 328, bypassing the data network 322. The mode of communication between the health monitoring device 320, the data processing terminal/PC 326, and the glucose monitor 324 and the data network 322 includes one or more wireless communication, wired communication, RF communication, BLUETOOTH® communication, WiFi data communication, radio frequency identification (RFID) enabled communication, ZIGBEE® communication, or any other suitable data communication protocol, and that optionally supports data encryption/decryption, data compression, data decompression and the like.

As described in further detail below, the physiological parameter analysis can be performed by one or more of the health monitoring device 320, data processing terminal/PC 326, glucose monitor 324, and server/cloud 328, with the resulting analysis output shared in the physiological parameter analysis system 310.

Additionally, while the glucose monitor 324, the health monitoring device 320, and the data processing terminal/PC 326 are illustrated as each operatively coupled to each other via communication links, they can be modules within one integrated device (e.g., sensor with a processor and communication interface for transmitting/receiving and processing data).

Measuring Glucose and HbA1c Levels

The measurement of the plurality of glucose levels through the various time periods described herein may be done with in vivo and/or in vitro (ex vivo) methods, devices, or systems for measuring at least one analyte, such as glucose, in a bodily fluid such as in blood, interstitial fluid (ISF), subcutaneous fluid, dermal fluid, sweat, tears, saliva, or other biological fluid. In some instances, in vivo and in vitro methods, devices, or systems may be used in combination.

Examples of in vivo methods, devices, or systems measure glucose levels and optionally other analytes in blood or ISF where at least a portion of a sensor and/or sensor control device is, or can be, positioned in a subject's body (e.g., below a skin surface of a subject). Examples of devices include, but are not limited to, continuous analyte monitoring devices and flash analyte monitoring devices. Specific devices or systems are described further herein and can be found in U.S. Pat. No. 6,175,752 and US Patent Application Publication No. 2011/0213225, the entire disclosures of each of which are incorporated herein by reference for all purposes In vitro methods, devices, or systems (including those that are entirely non-invasive) include sensors that contact the bodily fluid outside the body for measuring glucose levels. For example, an in vitro system may use a meter device that has a port for receiving an analyte test strip carrying bodily fluid of the subject, which can be analyzed to determine the subject's glucose level in the bodily fluid. Additional devices and systems are described further below.

As described above the frequency and duration of measuring the glucose levels may vary from, on average, about 3 times daily (e.g., about every 8 hours) to about 14,400 times daily (e.g., about every 10 seconds) (or more often) and from about a few days to over about 300 days, respectively.

Once glucose levels are measured, the glucose levels may be used to determine the one or more physiological parameters ($k_{gly}$, $k_{age}$, and/or K) and, optionally, other analyses (e.g., cHbA1c, personalized target glucose range, and others described herein). In some instance, such analyses may be performed with a physiological parameter analysis system. For example, referring back to FIG. 3, in some embodiments, the glucose monitor 324 may comprise a glucose sensor coupled to electronics for (1) processing signals from the glucose sensor and (2) communicating the processed glucose signals to one or more of health monitoring device 320, server/cloud 328, and data processing terminal/PC 326.

The measurement of one or more HbA1c levels at the various times described herein may be according to any suitable method. Typically, HbA1c levels are measured in a laboratory using a blood sample from a subject. Examples of laboratory tests include, but are not limited to, a chromatography-based assay, an antibody-based immunoassay, and an enzyme-based immunoassay. HbA1c levels may also be measured using electrochemical biosensors.

The frequency of HbA1c level measurements may vary from, on average, monthly to annually (or less often if the average glucose level of the subject is stable).

Once glucose levels are measured, the glucose levels may be used to determine the one or more physiological parameters and, optionally, other analyses described herein. In some instance, such analyses may be performed with a physiological parameter analysis system. For example, referring back to FIG. 3, in some embodiments, HbA1c levels may be measured with a laboratory test where the results are input to the server/cloud 328, the subject interface 320A, and/or a display from the testing entity, a medical professional, the subject, or other user. Then, the HbA1c levels may be received by the one or more of health monitoring device 320, server/cloud 328, and data processing terminal/PC 326 for analysis by one or more methods described herein.

Calculated HbA1c (cHbA1c)

After one or more physiological parameters ($k_{gly}$, $k_{age}$, and/or K) are calculated, a plurality of glucose measurements may be taken for a following time period and used for calculating HbA1c during and/or at the end of the following time period. For example, referring back to FIG. 1, one or more physiological parameters ($k_{gly}$, $k_{age}$, and/or K) may be calculated at time $t_1$ based on measurements of the plurality of glucose levels 104a over time period 106, a measured HbA1c level 102b at the end of time period 106, and optionally a measured HbA1c level 102a at the beginning of time period 106. Then, for a subsequent time period 108, a plurality of glucose levels 104b may be measured. Then, during and/or at the end of the time period 104b, Equation 8 can be used to determine a cHbA1c value (HbA1c$_z$ of Equation 8) where HbA1c$_0$ is the measured HbA1c level 102b at the end of time period 106 (which is the beginning of time period 108), [$G_i$] are the glucose levels or averaged glucose levels at times $t_i$ measured over time period 108 (or the portion of time period 108 where cHbA1c is determined during the time period 108), and the provided one or more physiological parameters ($k_{gly}$, $k_{age}$, and/or K) corresponding to time $t_1$ are used.

A subject's cHbA1c may be determined for several successive time periods based on the one or more physiological parameters ($k_{gly}$, $k_{age}$, and/or K) determined with the most recent measured HbA1c level and the intervening measurements of glucose levels. The HbA1c may be measured periodically (e.g., every 6 months to a year) to recalculate the one or more physiological parameters. The time between evaluating a measured HbA1c may depend on (1) the consistency of the measurements of glucose levels, (2) the frequency of the measurements of glucose levels, (3) a subject's and corresponding family's diabetic history, (4) the length of time the subject has been diagnosed with diabetes, (5) changes to a subject's personalized diabetes management (e.g., changes in medications/dosages, changes in diet, changes in exercise, and the like), and combinations thereof. For example, a subject with consistent measurements of glucose levels (e.g., a [G] with less than 5% variation) and frequent measurements of glucose levels (e.g., continuous glucose monitoring) may measure HbA1c levels less frequently than a subject who recently (e.g., within the last 6 months) changed the dosage of a glycation medication even with consistent and frequent measurements of glucose levels.

Figure 4:
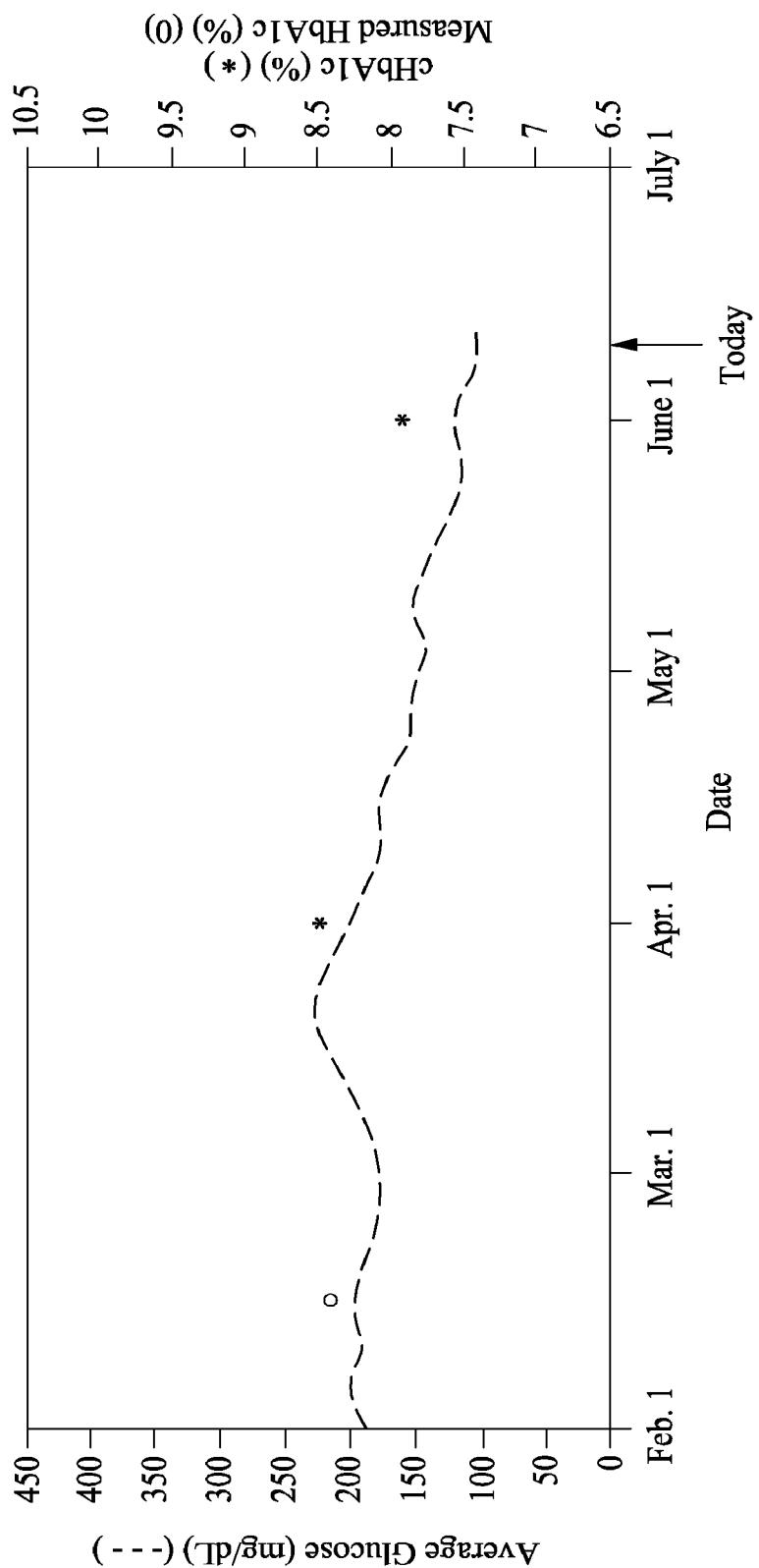
FIG. 4 illustrates an example of a cHbA1c report that may be generated as an output by a physiological parameter analysis system in accordance with some of the embodiments of the present disclosure.

FIG. 4, with reference to FIG. 2, illustrates an example of a cHbA1c report that may be generated as an output 218 by a physiological parameter analysis system 210 of the present disclosure. The illustrated example report includes a plot of average glucose level over time. Also included on the report is the most recently measured HbA1c level (open circle) and cHbA1c levels (asterisks) calculated by the physiological parameter analysis system 210. Two cHbA1c levels are illustrated, but one or more cHbA1c levels may be displayed on the report, including a line that continuously tracks cHbA1c. Alternatively, the output 218 of the physiological parameter analysis system 210 may include a single number for a current or most recently calculated cHbA1c, a table corresponding to the data of FIG. 4, or any other report that provides a subject, healthcare provider, or the like with at least one cHbA1c level.

In some instances, the cHbA1c may be compared to a previous cHbA1c and/or a previous measured HbA1c level to monitor the efficacy of a subject's personalized diabetes management. For example, if a diet and/or exercise plan is being implemented as part of a subject's personalized diabetes management, with all other factors (e.g., medication and other diseases) equal, then changes in the cHbA1c compared to the previous cHbA1c and/or the previous measured HbA1c level may indicate if the diet and/or exercise plan is effective, ineffective, or a gradation therebetween.

In some instances, the cHbA1c may be compared to a previous cHbA1c and/or a previous measured HbA1c level to determine if another HbA1c measurement should be taken. For example, in absence of significant glucose profile change, if the cHbA1c changes by 0.5 percentage units or more (e.g., changes from 7.0% to 6.5% or from 7.5% to 6.8%) as compared to the previous cHbA1c and/or the previous measured HbA1c level, another measured HbA1c level may be tested.

In some instances, a comparison of the cHbA1c to a previous cHbA1c and/or a previous measured HbA1c level may indicate if an abnormal or diseased physiological condition is present. For example, if a subject has maintained a cHbA1c and/or measured HbA1c level for an extended period of time, then if a change in cHbA1c is identified with no other obvious causes, the subject may have a new abnormal or diseased physiological condition. Indications of what that new abnormal or diseased physiological condition may be gleaned from the one or more physiological parameters ($k_{gly}$, $k_{age}$, and/or K). Details of abnormal or diseased physiological conditions relative to the one or more physiological parameters are discussed further herein.

Personalized-Target Glucose Range

Typically, the glucose levels in subjects with diabetes is preferably maintained between 54 mg/dL and 180 mg/dL. However, the kinetic model described herein (see Equation 6) illustrates that glucose levels are dependent on physiological parameters $k_{gly}$, $k_{age}$, and K. Therefore, a measured glucose level may not actually correspond to the actual physiological conditions in a subject. For example, a subject with a higher than normal K may glycate glucose more readily. Therefore, a 180 mg/dL measured glucose level may be too high for the subject and, in the long run, further continue the subject's diabetes. In another example, a subject with a lower than normal $k_{gly}$ may glycate glucose to a lesser degree. Accordingly, at a 54 mg/dL glucose level, the subject's intracellular glucose level may be much lower making the subject feel weak and, in the long term, lead to the subject being hypoglycemic.

Using the accepted normal lower glucose limit (LGL) and the accepted normal HbA1c upper limit (AU), equations for a personalized lower glucose limit (GL) (Equation 9) and a personalized upper glucose limit (GU) (Equation 10) can be derived from Equation 6.

$$GL = (LGL * k_{gly}^{ref}) / k_{gly}^{sub} \qquad \text{Equation 9}$$

where $k_{gly}^{ref}$ is the $k_{gly}$ for a normal person and $k_{gly}^{sub}$ is the subject's $k_{gly}$.

$$GU = AU / (K(1-AU)) \qquad \text{Equation 10}$$

Equation 9 is based on $k_{gly}$ because the lower limit of a glucose range is based on an equivalent intracellular glucose level. Equation 10 is based on K because the upper limit of a glucose range is based on an equivalent extracellular glucose level (e.g., the accepted normal HbA1c upper limit).

The currently accepted values for the foregoing are LGL=54 mg/dL, $k_{gly}^{ref}$=6.2*10$^{-6}$ dL*mg$^{-1}$*day$^{-1}$, and AU=0.08 (i.e., 8%). Using the currently accepted values Equations 11 and 12 can be derived.

$$GL = 3.35 * 10^{-4} \text{ day}^{-1} / k_{gly}^{sub} \qquad \text{Equation 11}$$

$$GU = 0.087/K \qquad \text{Equation 12}$$

Figure 5A:
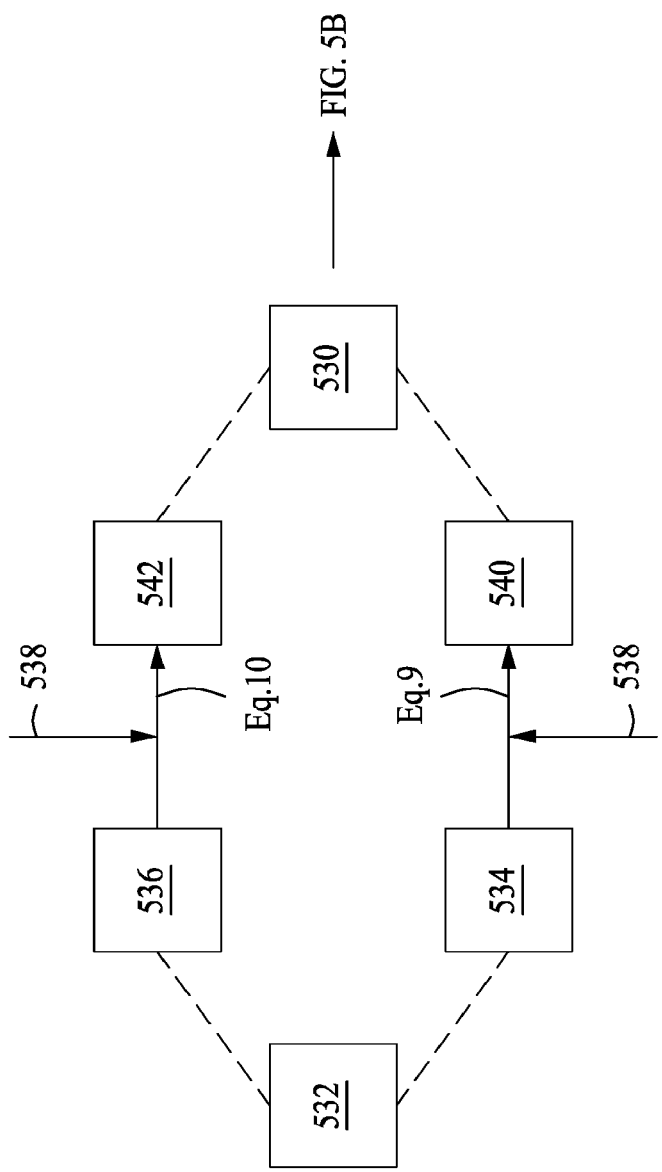
FIG. 5A illustrates an example of a method of determining a personalized-target glucose range in accordance with some of the embodiments of the present disclosure.

FIG. 5A illustrates an example of a method of determining a personalized-target glucose range 530. A desired intercellular glucose range 532 (e.g., the currently accepted glucose range) having a lower limit 534 and an upper limit 536 can be personalized using one or more determined physiological parameters ($k_{gly}$, $k_{age}$, and/or K) 538 using Equation 9 and Equation 10, respectively. This results in a personalized lower glucose limit (GL) 540 (Equation 9±7%) and a personalized upper glucose limit (GU) 542 (Equation 10±7%) that define the personalized-target glucose range 530. After one or more physiological parameters ($k_{gly}$, $k_{age}$, and/or K) are calculated, a personalized-target glucose range may be determined where the lower glucose limit may be altered according to Equation 9 (or Equation 11)±7% and/or the upper glucose limit may be altered according to Equation 10 (or Equation 12)±7%.

For example, a subject with a K of 4.5*10$^{-4}$ dL/mg and a $k_{gly}$ of 7.0*10$^{-6}$ dL*mg$^{-1}$*day$^{-1}$ may have a personalized-target glucose range of about 48±3.5 mg/dL to about 193±13.5 mg/dL. Therefore, the subject may have a wider range of acceptable glucose levels than the currently practiced glucose range.

Figure 5B:
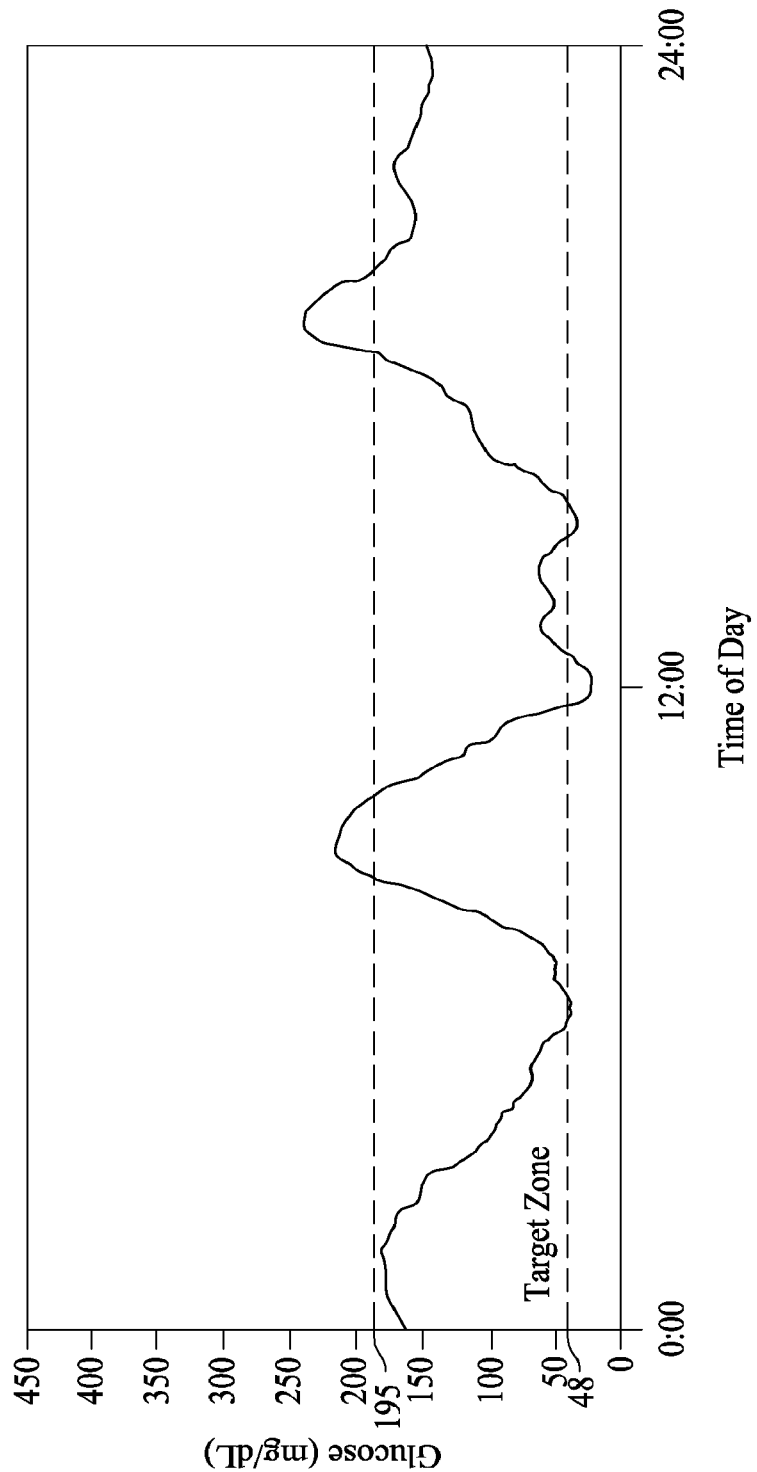
FIG. 5B illustrates an example of a personalized-target glucose range report that may be generated as an output by a physiological parameter analysis system in accordance with some of the embodiments of the present disclosure.

FIG. 5B, with reference to FIG. 2, illustrates an example of a personalized-target glucose range report that may be generated as an output 218 by a physiological parameter analysis system 210 of the present disclosure. The illustrated example report includes a plot of glucose level over a day relative to the foregoing personalized-target glucose range (shaded area). Alternatively, other reports may include, but are not limited to, an ambulatory glucose profile (AGP) plot, a numeric display of the personalized-target glucose range with the most recent glucose level measurement, and the like, and any combination thereof.

In another example, a subject with a K of 6.5*10$^{-4}$ dL/mg and a $k_{gly}$ of 6.0*10$^{-6}$ dL*mg$^{-1}$*day$^{-1}$ may have a personalized-target glucose range of about 51±3.5 mg/dL to about 145±10 mg/dL. With the much-reduced upper glucose level limit, the subject's personalized diabetes management may include more frequent glucose level measurements and/or medications to stay substantially within the personalized-target glucose range.

In yet another example, a subject with a K of 5.0*10$^{-4}$ dL/mg and a $k_{gly}$ of 5.0*10$^{-6}$ dL*mg$^{-1}$*day$^{-1}$ may have a personalized-target glucose range of about 67±4.5 mg/dL to about 174±12 mg/dL. This subject is more sensitive to lower glucose levels and may feel weak, hungry, dizzy, etc. more often if the currently practiced glucose range (54 mg/dL and 180 mg/dL) were used.

While the foregoing example all include a personalized glucose lower limit and a personalized glucose upper limit, personalized-target glucose range may alternatively include only the personalized glucose lower limit or the personalized glucose upper limit and use the currently practiced glucose lower or upper limit as the other value in the personalized-target glucose range.

The personalized-target glucose range may be determined and/or implemented in a physiological parameter analysis system. For example, a set of instructions or program associated with a glucose monitor and/or health monitoring device that determines a therapy (e.g., an insulin dosage) may use a personalized-target glucose range in such analysis. In some instances, a display or subject interface with display may display the personalized-target glucose range.

The personalized-target glucose range may be updated over time as one or more physiological parameters are recalculated.

Personalized-Target Average Glucose

In some instances, a subject's personalized diabetes management may include having a HbA1c value target for a future time point. For example, referring to FIG. 1, a subject may have a measured HbA1c value 102b for time $t_1$ and a plurality of glucose level measurements prior thereto over time period 106. The subject's personalized diabetes management may include a target HbA1c value (AT) for time $t_2$ that would correlate to improved health for the subject. Equation 13 can be used to calculate a personalized-target average glucose level (GT) for the next time period 108 and be based on the target HbA1c value (AT) and the subject's K calculated at time $t_1$.

$$GT = AT / (K(1-AT)) \qquad \text{Equation 13}$$

In some embodiments, a physiological parameter analysis system may determine an average glucose level for the subject during time period 108 and, optionally, display the average glucose level and/or the target average glucose level. The subject may use the current average glucose level and the target average glucose level to self-monitor their progress over time period 108. In some instances, the current average glucose level may be transmitted (periodically or regularly) to a health care provider using a physiological parameter analysis system for monitoring and/or analysis.

Figure 6:
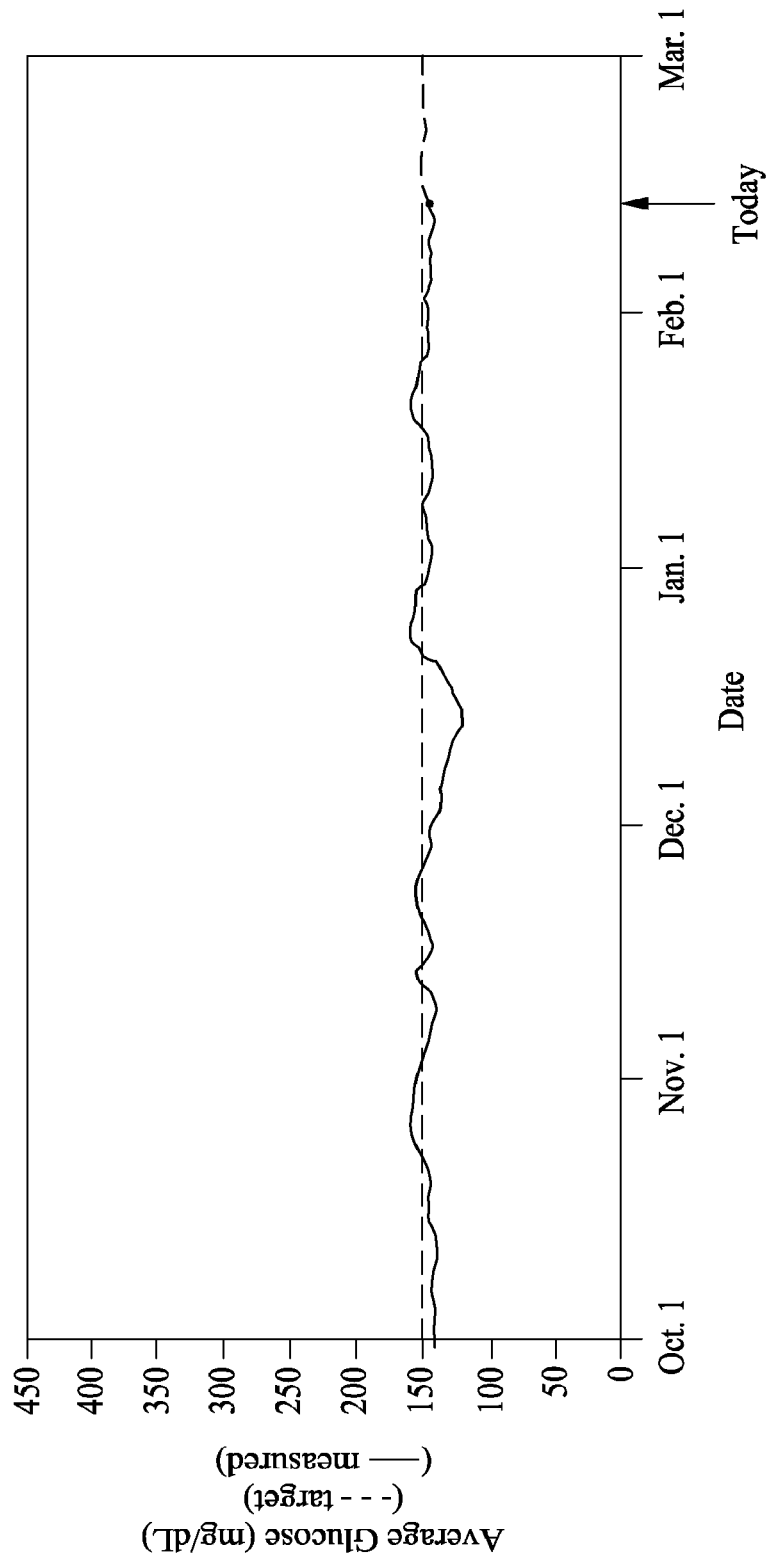
FIG. 6 illustrates an example of a personalized-target average glucose report that may be generated as an output by a physiological parameter analysis system in accordance with some of the embodiments of the present disclosure.

FIG. 6, with reference to FIG. 2, illustrates an example of a personalized-target average glucose report that may be generated as an output 218 by a physiological parameter analysis system 210 of the present disclosure. The illustrated example report includes a plot of a subject's average glucose (solid line) over time and the personalized-target average glucose (illustrated at 150 mg/dL, dashed line). Alternatively, other reports may include, but are not limited to, a numeric display of the personalized-target average glucose with the subject's average glucose level over a given time frame (e.g., the last 12 hours), and the like, and any combination thereof.

The personalized-target average glucose may be updated over time as one or more physiological parameters are recalculated.

Personalized Treatment—Subject Triage

Insulin pumps along with continuous glucose monitoring may be used for subjects that need tight control of their glucose levels. As illustrated above, the target glucose range is individualized and based on $k_{gly}$ and/or K. Therefore, in some instances, subjects with a narrower personalize-target glucose range may be stronger candidates for insulin pumps with continuous monitoring. Triage of subjects to be stronger candidates for insulin pumps along with continuous glucose monitoring may be based on a spread of the personalized-target glucose range, $k_{gly}$, and/or K.

The spread between currently practiced glucose lower or upper limit is about 126 mg/dL. However, as illustrated above, depending on $k_{gly}$ and K that could narrow to about 94 mg/dL. Some embodiments may involve triaging a subject to an insulin pump with continuous glucose monitoring when the personalized-target glucose range span is about 110 mg/dL or less, preferably about 100 mg/dL or less.

Some embodiments may involve triaging a subject to an insulin pump with continuous glucose monitoring when $k_{gly}$ is $6.4*10^{-6}$ dL*mg$^{-1}$*day$^{-1}$ or less, when $k_{gly}$ is $6.0*10^{-6}$ dL*mg$^{-1}$*day$^{-1}$ or less, when $k_{gly}$ is $5.5*10^{-6}$ dL*mg$^{-1}$*day$^{-1}$ or less, or when $k_{gly}$ is $5.0*10^{-6}$ dL*mg$^{-1}$*day$^{-1}$.

Some embodiments may involve triaging a subject to an insulin pump with continuous glucose monitoring when K is $5.0*10^{-4}$ dL/mg or greater, when K is $5.5*10^{-4}$ dL/mg or greater, when K is $5.75*10^{-4}$ dL/mg or greater, or when K is $6.0*10^{-4}$ dL/mg or greater.

In some embodiments, triaging a subject to an insulin pump with continuous glucose monitoring may be a stepped triage where first a subject's glucose levels are monitored continuously for a reasonable time period (e.g., about 5 days, about 10 days, about 15 days, about 30 days, or more). This continuous monitoring time period can be used to assess if the subject is capable of managing glucose levels effectively or if an insulin pump is better, or required.

Whether the triaging is straight to an insulin pump with continuous glucose monitoring or a stepped triage with monitoring before treatment with the insulin pump may be determined by the level of the indicators (i.e., the personalized-target glucose range span, $k_{gly}$, K, or any combination thereof). For example, if $k_{gly}$ is about $6.4*10^{-6}$ dL*mg$^{-1}$*day$^{-1}$ but the personalized-target glucose range span is about 100 mg/dL, the subject may be more suited for a stepped triage as compared to another subject where the corresponding indicators suggest an insulin pump should be used.

In some embodiments, triage may be based on a lookup table (e.g., stored in a physiological parameter analysis system of the present disclosure). The lookup table may, for example, correlate multiple values to each other including, but not limited to, one or more physiological parameters ($k_{gly}$, $k_{age}$, and/or K), a personalized-target glucose range span, and/or other factors described herein like an existing medical condition, a family history of a medical condition, a current treatment, an age, a race, a gender, a geographic location, a diabetes type, a duration of diabetes diagnosis, and the like, and any combination thereof. Columns in the lookup table may, for example, define ranges or limits for the foregoing parameters, and the rows may indicate a suggested course of action, which may be an output 218 of a physiological parameter analysis system 210 of FIG. 2. For example, two columns may define an upper and lower bound of $k_{gly}$, where each row corresponds to a suggested course of action, such as "candidate for insulin pump," "candidate for closed-loop control system," "candidate for basal/bolus insulin therapy," "candidate for basal only insulin therapy," or any such treatment used to control diabetes or effect the subject's glycation. In some instances, more than one course of action may be indicated. Therefore, in this example, a subject triage report may simply display the suggested course(s) of action.

Alternatively, the subject triage report may, for example, show a map of zones corresponding to the course(s) of action on a plot defined by one or more of the parameters described above relative to the lookup table. Such zones may, in some instances, be defined by the lookup table, labeling each zone representing a recommendation and indicated the glycemic parameter point on the map to show the relevant zone for that subject.

While the two foregoing subject triage reports are examples based on lookup tables, alternatively, the two foregoing subject triage reports could be based on other correlations between (1) one or more physiological parameters ($k_{gly}$, $k_{age}$, and/or K), a personalized-target glucose range span, and/or other factors described herein and (2) a course(s) of action (e.g., a mathematical algorithm or matrix analysis).

As described, a subject's glycation parameters may help healthcare providers and payors to better determine what therapy tools are most appropriate for which subjects. For instance, closed-loop insulin pump systems are expensive to employ and maintain, but subjects who have a high glycation rate may have a very narrow personalized-target glucose range where the safest treatment is keeping their glucose levels within such ranges using a closed-loop insulin pump system.

In some embodiments, the insulin pumps along with continuous glucose monitoring may be closed-loop systems. In some embodiments, the insulin pumps along with continuous glucose monitoring may be hybrid-loop systems. For example, referring back to FIG. 3, a physiological parameter analysis system may further include one of the foregoing insulin pumps communicable with one or more of the components in the physiological parameter analysis system 310, for example, the glucose monitor 324 (e.g., a continuous glucose monitoring system) and health monitoring device 320.

Personalize Treatment—Titration of Diabetes Medication

In some embodiments, one or more physiological parameters ($k_{gly}$, $k_{age}$, and K) may be used in titrating dosages of diabetes medication (e.g., insulin) to a subject. For example, referring to FIG. 2, a physiological parameter analysis system 210 of the present disclosure may determine or have input (1) one or more physiological parameters, (2) a personalized-target glucose range, and/or (3) a personalized-target average glucose. Then, when a subsequent glucose level is measured the physiological parameter analysis system 210 may output a recommended diabetes medication dosage. An alternative or complimentary output 218 may be a glucose pattern insight report.

Examples of glucose pattern insight reports can be found in US Patent Application Publication Nos. 2014/0188400 and 2014/0350369, each incorporated herein by reference. The disclosed analyses and reports in the forgoing applications may be modified based on the one or more physiological parameters ($k_{gly}$, $k_{age}$, and K) of the present disclosure.

Figure 7:
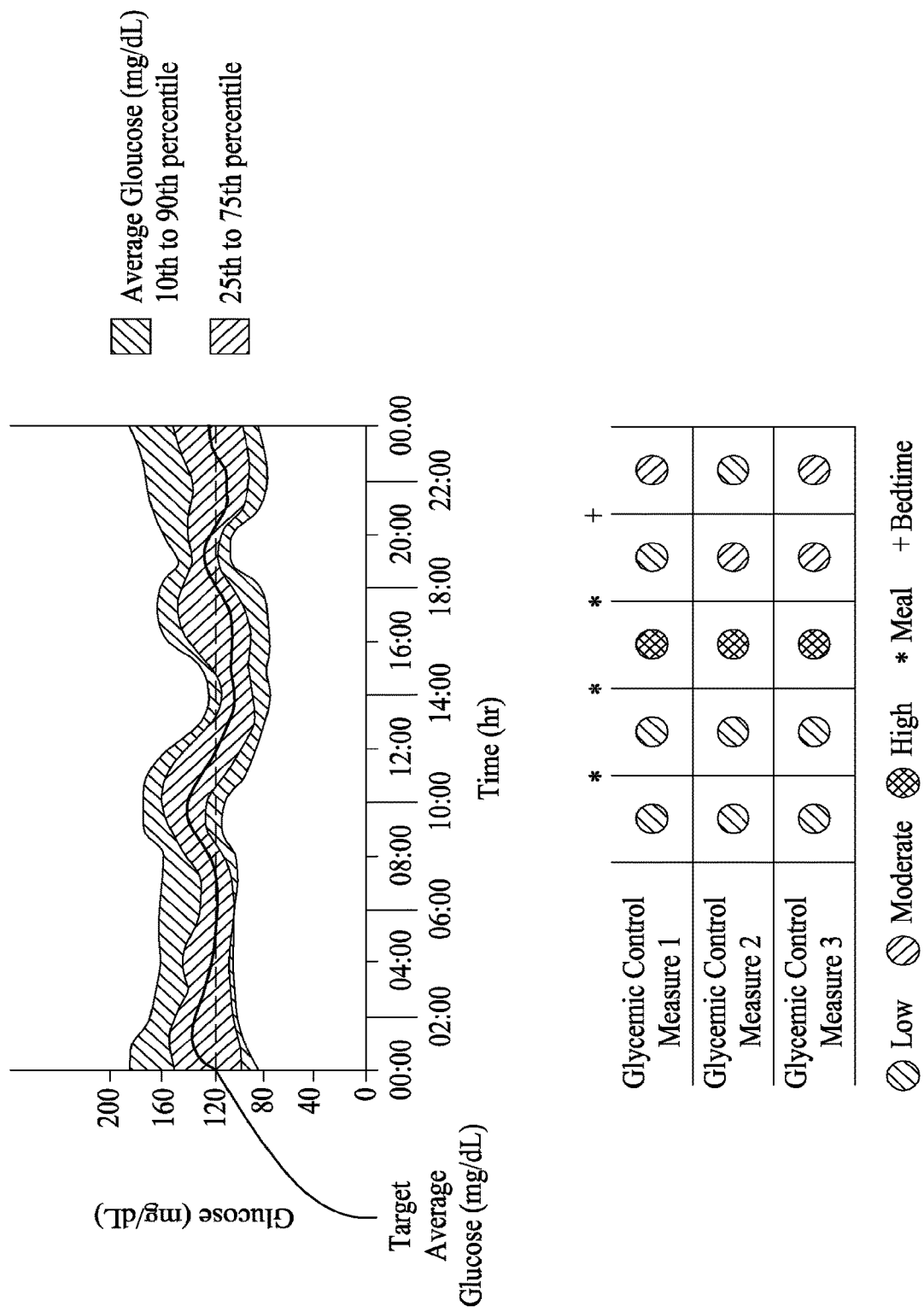
FIG. 7 illustrates an example of a glucose pattern insight report that may be generated as an output by a physiological parameter analysis system in accordance with some of the embodiments of the present disclosure.

For example, FIG. 7, with reference to FIG. 2, illustrates an example of a glucose pattern insight report that may be an output 218 of a physiological parameter analysis system 210 (e.g., an insulin titration system). The illustrated glucose pattern insights report incorporates an AGP along with a table of glycemic control measures (or "traffic lights"). As illustrated, the report includes an AGP plot over an analysis time period (e.g., about one to about four months) that illustrates the personalized-target average glucose at 120 mg/dL, the average glucose levels for the subject over the analysis time period, the 25$^{th}$ to 75$^{th}$ percentile of glucose levels for the subject over the analysis time period, and the 10$^{th}$ to 90$^{th}$ percentile of glucose levels for the subject over the analysis time period. Optionally, the glucose pattern insight report may further or alternatively display the personalized-target glucose range. Additionally, the glucose pattern insight report may optionally further include one or more of: a measured HbA1c level, a cHbA1c level, the date range over which the average glucose and related percentiles were determine, and the like.

Below the AGP plot on the glucose pattern insight report is the table that correlates one or more (illustrated as three) glycemic control measures to a subject's average glucose levels for a given shortened time period of the day over the analysis time period. The correlation displays, in this example, as traffic lights (e.g., green (good), yellow (moderate), or high (red)) that correspond to the risk of a condition based on the glycemic control measures. Examples of glycemic control measures include, but are not limited to, likelihood of low glucose, likelihood of high glucose, the proximity of the average glucose to the personalized-target average glucose, the adherence of the glucose levels to the personalized-target glucose range, the degree of variability of the average glucose below (or above) to the personalized-target average glucose, the degree of variability of the glucose levels outside (below and/or above) the personalized-target glucose range, and the like.

In some embodiments, the glucose pattern insights report may be used as part of a diabetes medication titration system, where the traffic lights (or values associated therewith) can drive logic to provide treatment modifications such as changing basal dosages of the diabetes medication or bolus amounts of the diabetes medication associated with meals. For example, when used in conjunction with an automatic or semi-automatic system for titration, the logic driving these traffics lights may provide recommendations to subjects on dosage adjustments.

The glucose pattern insights report and related analyses that incorporate the use of the kinetic model described herein may provide better treatment to subjects with diabetes. For this example, as described above, a subject with a K of $5.0*10^{-4}$ dL/mg and a $k_{gly}$ of $5.0*10^{-6}$ dL*mg$^{-1}$*day$^{-1}$ may have a personalized-target glucose range of about 67±4.5 mg/dL to about 174±12 mg/dL. This subject is more sensitive to lower glucose levels and may feel weak, hungry, dizzy, etc. more often if the currently practiced glucose range (54 mg/dL and 180 mg/dL) were used. The analytical logic used for the glucose pattern insights report described herein that uses one or more physiological parameters ($k_{gly}$, $k_{age}$, and K) may include settings that define the risk of hypoglycemia as traffic lights for "likelihood of low glucose." For example, if the likelihood of low glucose indicates low risk (e.g., a green traffic light), then it is considered safe to increase insulin. If the likelihood of low glucose indicates moderate risk (e.g., yellow traffic light), then it is considered that the current risk is acceptable but no further increase of insulin should be made. Finally, if the likelihood of low glucose indicates high risk, then it is recommended that insulin should be reduced to get the glucose back to tolerable levels. For a subject with high risk of hypoglycemia because of an increase lower glucose level threshold, the amount of risk associated with moderate and high risk (e.g., how far below the lower glucose level threshold) may be less than a subject with a normal lower glucose level threshold.

While the foregoing example discusses a glucose pattern insights report as the output 218, other outputs using the same logic and analyses may be used in other embodiments. For example, the output 218 may be values of dosage recommendations.

The one or more physiological parameters ($k_{gly}$, $k_{age}$, and K) and related analyses (e.g., personalized-target glucose range, personalized-target average glucose, cHbA1c, and the like) may be updated periodically (e.g., about every 3 months to annually). The frequency of updates may depend on, among other things, the subject's glucose level and diabetes history (e.g., how well the subject stays within the prescribed thresholds), other medical conditions, and the like.

An insulin titration system may optionally also utilize error associated with the one or more physiological parameters ($k_{gly}$, $k_{age}$, and K). Error values can be determine using standard statistically techniques by those skilled in the art and may be used as another set of parameters for configuring the titration system. For example, the titration system may use the reduced amount of risk for hypoglycemia (i.e., a smaller tolerance to be below the lower glucose level threshold for indicating moderate and high risk) may be implemented when the lower glucose level of the personalized-target glucose range of about 64 mg/dL with an error of about 7% or less.

The dosage of diabetes mediation (e.g., via titration) may be updated over time as one or more physiological parameters are recalculated.

Closed-Loop and Hybrid Closed-Loop Control Systems

Closed-loop systems and hybrid closed-loop systems that recommend or administer insulin dosages to a subject have been developed for insulin delivery based on near real-time glucose readings. These systems are often based on models describing the subject's physiology, glucose sensor dynamics, and glucose sensor error characteristics. In some embodiments, the one or more physiological parameters ($k_{gly}$, $k_{age}$, and K) and related analyses (e.g., personalized-target glucose range, personalized-target average glucose, cHbA1c, and the like) may be incorporated into the closed-loop system, similarly to what was described above for insulin titration, in order to better meet the needs of the subject.

Closed-loop systems often are configured to "drive" the subject's glucose levels inside a target range and/or toward a single glucose target, which may be the personalized-target glucose range and/or the personalized-target average glucose described herein. For example, for a subject with high $k_{gly}$ and an increased lower glucose limit for their personalized-target glucose range, the controller may drive their glucose levels in a way to stay above the lower glucose limit based on $k_{gly}$, which avoids lower glucose levels that adversely affect them more than subjects with a normal glucose range. Similarly, subjects with reduced upper glucose limits for their personalized-target glucose range may have the controller of a closed-loop insulin delivery system and hybrid closed-loop insulin delivery system drive glucose to stay below the personalized-upper glucose limit to mitigate hyperglycemic effects.

The metrics by which a closed-loop insulin delivery system and hybrid closed-loop insulin delivery system determine a dosage of insulin may be updated over time as one or more physiological parameters are recalculated. For example, the personalized-target glucose range and/or personalized-target average glucose may be updated when one or more physiological parameters are recalculated.

Personalized Treatment—Glycation Medication

Diabetes is a disease caused by a subject's pancreas being unable to produce sufficient (or any) insulin. However, in some instances, a subject's glycation process may be the source of the body not properly controlling intracellular glucose. Such subjects may be more responsive to treatments that use glycation-medications rather than traditional diabetes treatments. The kinetic model of the present disclosure derives $k_{gly}$ and/or K (which is based in part on $k_{gly}$). Therefore, one or both of these physiological parameters may be used in identifying, treating, and/or monitoring a subject with a glycation disorder.

Some embodiments may involve monitoring $k_{gly}$ and/or K for a subject on glycation medication and, optionally, changing a glycation medication dosage based on changes to $k_{gly}$ and/or K. For example, referring to FIG. 1, some embodiments may involve determining $k_{gly1}$ and/or $K_1$ at a time $t_1$ and a corresponding $k_{gly2}$ and/or $K_2$ at time $t_2$ (as described above) and treating a subject with glycation medication over time period 108. Then, based on a comparison of $k_{gly1}$ and/or $K_1$ to the corresponding $k_{gly2}$ and/or $K_2$, a dosage and/or type of glycation medication may be altered for a subsequent time period. Then, in some instances, a corresponding $k_{gly3}$ and/or $K_3$ may be determined at the end of the subsequent time period for comparison to one or more of the previously determined physiological parameters. The time between $t_1$ and $t_2$ and between $t_2$ and $t_3$ should be at least the expected time for the glycation medication to make a measurable change in the parameter being monitored, which may depend on the medication and the dosage.

In some embodiments, an output 218 of the physiological parameter analysis system 210 of FIG. 2 may be a glycation medication report that includes glycation medication and/or dosage recommendations based on $k_{gly}$ and/or K calculated by the physiological parameter analysis system 210. This output 218 may be displayed for a subject, healthcare provider, and/or the like to review and adjust the glycation medication and/or dosage.

Alternatively, the dosage recommendations provide a subject and/or automated medication delivery system with the next dosage to be administered. Here, the system guides titration of the medication, where the subject may start with the lowest dosage or a recommended initial dosage. The initial dosage may be defined by the current condition of the subject, the subject's $k_{gly1}$ and/or $K_1$, and other factors described herein. After an appropriate amount of time has passed for the effects of the current medication dosage to be adequately determined, $k_{gly2}$ and/or $K_2$ can be determined based on a new measured HbA1c level and the glucose levels measured during the medication dosage. $k_{gly2}$ and/or $K_2$ may then be compared to (1) $k_{gly1}$ and/or $K_1$ and/or (2) a target $k_{gly}$ and/or a target K to determine if the dosage needs to be changed. For example, for a high glycator subject taking a medication is intended to lower glycation rate, if $k_{gly2}$ is still higher than desired, then the dosage recommendation may be increased according to (1) standard titration protocols and/or (2) a system that accounts for how past dosage changes affect the subject (known as control theory). In another example, if the subject's $k_{gly2}$ is low, then the dosage may be decreased. Medications could also be similarly titrated to affect K or other parameters. In addition, a similar process could be used to recommend non-medication treatments such as blood transfusion or harvesting by guiding the appropriate amount of blood to be affected.

Using $k_{gly}$ and/or K to monitor glycation medication efficacy and titration is valuable to healthcare providers for treating subjects with abnormal glycation physiology.

The metrics by which a dosage of glycation medication is determined may be updated over time as one or more physiological parameters are recalculated.

Identifying Abnormal or Diseased Physiological Condition

The kinetic modeling, in certain embodiments, provides physiological parameters (e.g., $k_{gly}$, $k_{age}$ (or $k_{gen}$), and/or K) for different time periods, where the same parameter is compared between the different time periods to indicate abnormal or disease state of the subject. Variation in the $k_{gly}$, $k_{age}$, and/or K in subjects may provide an indication of abnormal or disease condition of the subject. That is, while $k_{gly}$, $k_{age}$, and/or K varies between subjects, a variation in $k_{gly}$, $k_{age}$, and/or K for a single individual are small and slow. Thus, a comparison of $k_{gly}$, $k_{age}$, and/or K at two or more different time periods provides physiological condition information of the subject. For example, when a clinically significant change to $k_{gly}$, $k_{age}$, and/or K is observed over time an abnormal or diseased physiological condition may, and likely, exists.

For example, when $k_{gly}$ significantly varies over time such that the variation is clinically significant, such clinically significant variation can indicate that the glucose transporter level or cell membrane has changed. Such biological changes may indicate a potential metabolic change in the subject's body resulting from the subject's physiology under-going a disease state.

When $k_{age}$ and/or $k_{gen}$ varies significantly over time such that the variation is clinically significant, such clinically significant variation can indicate changes to the subject's immune system because the immune system is designed to recognize cells that need to be removed.

A clinically significant variation in $k_{age}$ and/or $k_{gen}$ may also or alternatively be associated with the oxygen sensing mechanism in the body. An increasing $k_{age}$ and/or $k_{gen}$ over time may indicate that the subject's body needs the red blood cells to carry more oxygen or the oxygen sensing mechanism is not functioning correctly, either reason indicating a physiological state change such as for example, blood loss or a disease condition.

In yet another example (in combination or alternative of the foregoing examples), clinically significant variation in $k_{age}$ and/or $k_{gen}$ may be associated with bone marrow changes. For example, if the bone marrow suddenly produces a lot more oxygen carrying red blood cells, the subject's body will respond by killing off or eliminating more red blood cells. That is, a clinically significant increase in $k_{age}$ and/or $k_{gen}$ may be associated with bone marrow abnormality.

In another example, a hormone disorder can cause a clinically significant variation in $k_{age}$, $k_{gen}$, and K. Hormones can affect heart rate, contraction strength, blood volume, blood pressure, and red blood cell production. Stress hormones such as catecholamines and cortisol stimulate the release of reticulocytes from the bone marrow and possibly also enhance erythropoiesis. Therefore, large fluctuation on hormone level can change $k_{age}$ and/or $k_{gen}$, and consequently K.

In yet another example, deviations from normal of the $k_{gly}$, $k_{age}$, and/or K may be an indicator of diabetes or pre-diabetes. Using $k_{gly}$, $k_{age}$, and/or K to measure diabetes or pre-diabetes may be more effective than standard fasting glucose tests and measured HbA1c. For instance, a subject with a measured HbA1c value in the normal range and normal fasting glucose may have low $k_{gly}$ associated with high glucose values at times in the day other than fasting. Therefore, the subject may be a candidate for earlier diabetes intervention that otherwise may have gone unnoticed based on standard diabetes diagnoses methods.

In another example, for a subject with a newly high measured HbA1c, the standard diabetes treatments may be employed to lower their HbA1c. However, determining that $k_{gly}$ is abnormal may be an indication that the problem with their glycation physiology rather than their pancreas, suggesting other more targeted forms of treatment.

Embodiments of the present disclosure include displaying the determined $k_{gly}$, $k_{age}$, and/or K, the changes in $k_{gly}$, $k_{age}$, and/or K over time, and/or possible abnormal or diseased physiological conditions.

In the manner described herein, in accordance with the embodiments of the present disclosure, the physiological parameter analysis provides an indication of a subject's abnormal or disease condition, as well as an analysis and/or monitoring tool for one or more parameters or characteristics for a subject's personalized diabetes management.

Identifying Supplements and/or Medicines

Several supplements and medications interact with the kinetics of red blood cell glycation, elimination, and generation within the body. For example, supplements and medicines used by athletes to dope include, but are not limited to, human growth hormones, supplements and medicines that increase metabolic levels, and the like. Human growth hormones can increase red blood cell count and, consequently, increase $k_{age}$. In another example, supplements and medicines that increase metabolic levels (e.g., exercise mimetics like AMPK agonists) can affect $k_{gly}$. Therefore, some embodiments may use one or more physiological parameters ($k_{gly}$, $k_{age}$, and/or K) as an indicator of doping.

In a first example, having one or more physiological parameters ($k_{gly}$, $k_{age}$, and/or K) outside normal ranges may be used, in some instances, as an indicator of doping.

In another example, once the one or more physiological parameters ($k_{gly}$, $k_{age}$, and/or K) are determined, continuous monitoring over a 10-day or longer period could identify sudden changes in the physiological parameters that could indicated doping. This could be used alone or in combination with the foregoing example of the one or more physiological parameters being outside normal ranges.

Physiological Age

The physiological parameters $k_{age}$ and, consequently, K change due to aging. Therefore, $k_{age}$ and/or K (provided a stable or known change in $k_{gly}$) may be used as biological markers to calculate a standardized metabolic age. Generally, over time, $k_{age}$ decreases and K increases. Using a correlation between $k_{age}$ and/or K and age in healthy subjects, a new subject's metabolic age may be calculated. This metabolic age may then be used as an indicator of the new subject's risk for age-related degenerative conditions like heart disease, Alzheimer's, or osteoperosis. The risk for age-related degenerative conditions may be used in conjunction with family history of age-related degenerative conditions for proactive screening and/or preventive treatment. For example, a 54-year old subject with a metabolic age of 65 with a family history of cardiovascular disease developing later in life may be tested more often for signs and/or progression of cardiovascular disease than a 54-year old subject with a metabolic age of 50 and a similar family history.

Analyte Monitors and Monitoring Systems

Generally, embodiments of the present disclosure are used with or as systems, devices, and methods for measuring glucose and, optionally, at least one other analyte in a bodily fluid. The embodiments described herein can be used to monitor and/or process information regarding glucose and, optionally, at least one other analyte. Other analytes that may be monitored include, but are not limited to, glucose derivatives, HbA1c, acetyl choline, amylase, bilirubin, cholesterol, chorionic gonadotropin, creatine kinase (e.g., CK-MB), creatine, creatinine, DNA, fructosamine, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor glucose and one or more than one analytes, each of the analytes may be monitored at the same or different times.

The analyte monitors and/or analyte monitoring systems (referred to herein collectively as analyte monitoring systems) used with or as systems, devices, and methods for measuring glucose and, optionally, one or more analytes in a bodily fluid may be in vivo analyte monitoring systems or in vitro analyte monitoring systems. In some instances, systems, devices, and methods of the present disclosure may use both in vivo analyte monitoring systems and in vitro analyte monitoring systems.

In vivo analyte monitoring systems include analyte monitoring systems where at least a portion of an analyte sensor is, or can be, positioned in the body of a subject to obtain information about at least one analyte of the body. In vivo analyte monitoring systems can operate without the need for a factory calibration. Examples of in vivo analyte monitoring systems include, but are not limited to, continuous analyte monitoring systems and flash analyte monitoring systems.

Continuous analyte monitoring systems (e.g., continuous glucose monitoring systems), for example, are in vivo systems that can transmit data from a sensor control device to a reader device repeatedly or continuously without prompting (e.g., automatically according to a schedule).

Flash analyte monitoring systems (or flash glucose monitoring systems or simply flash systems), for example, are in vivo systems that can transfer data from a sensor control device in response to a scan or request for data by a reader device, such as with a near field communication (NFC) or radio frequency identification (RFID) protocol.

In vivo analyte monitoring systems can include a sensor that, while positioned in vivo, makes contact with the bodily fluid of the subject and senses one or more analyte levels contained therein. The sensor can be part of a sensor control device that resides on the body of the subject and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric. The term "on body" refers to any device that resides directly on the body or in close proximity to the body, such as a wearable device (e.g., glasses, watch, wristband or bracelet, neckband or necklace, etc.).

In vivo analyte monitoring systems can also include one or more reader devices that receive sensed analyte data from the sensor control device. These reader devices can process and/or display the sensed analyte data, in any number of forms, to the subject. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

For example, referring to FIG. 3, a sensor or portion thereof of an in vivo analyte monitoring system may be the glucose monitor 324, and the reader device may be the health monitoring device 320. In alternative embodiments, the in vivo analyte monitoring system may be, in whole, the glucose monitor 324 that transmits data to a health monitoring device 320, data network 322, data processing terminal/PC 326, and/or server/cloud 328.

For in vivo analyte monitoring systems, the determination of one or more physiological parameters (e.g., $k_{gly}$, $k_{age}$ (or $k_{gen}$), and/or K) and/or other analyses described herein may be performed within the in vivo analyte monitoring system, in some instances. Only the physiological parameters may, for example, be determined within the in vivo analyte monitoring system and transmitted to a suitable other component of a physiological parameter analysis system, which may perform other analyses described herein. In some embodiments, the in vivo analyte monitoring system may only produce output signals that correspond to glucose levels that are received by another component of a physiological parameter analysis system. In such cases, one or more of the other component(s) of the physiological parameter analysis system may determine one or more physiological parameters (e.g., $k_{gly}$, $k_{age}$ (or $k_{gen}$), and/or K) and, optionally, perform one or more of the other analyses described herein.

Figure 8:
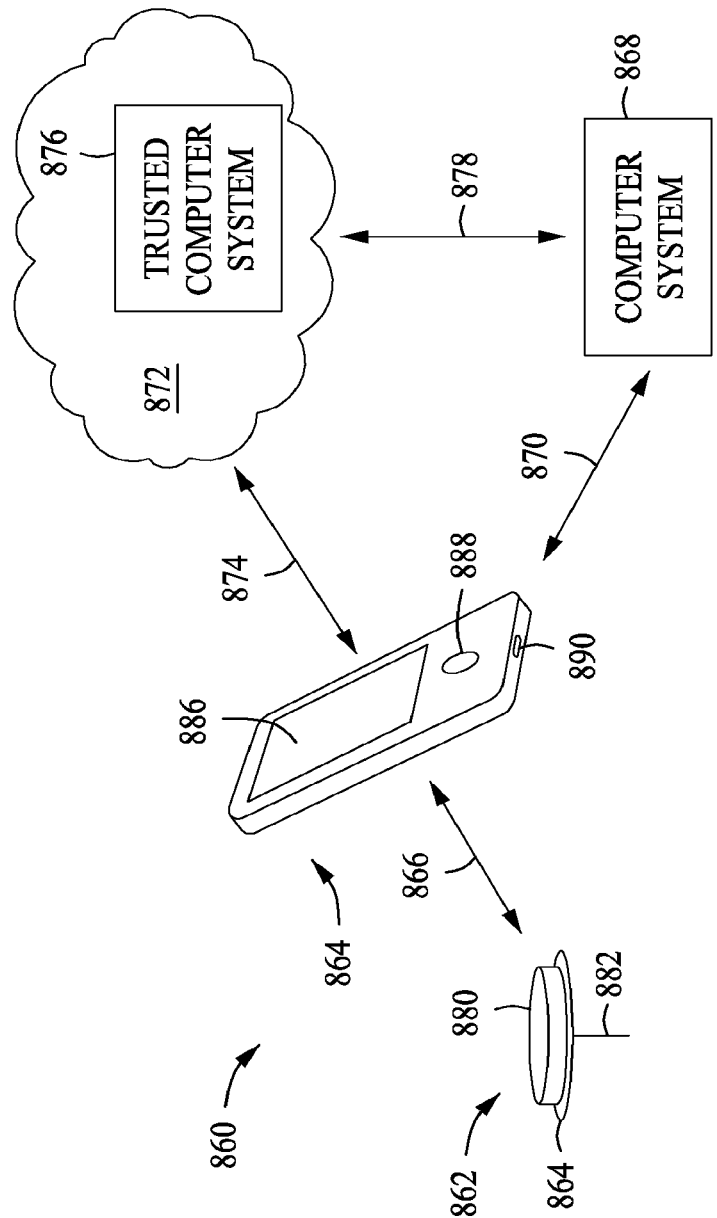
FIG. 8 illustrates an example of an in vivo analyte monitoring system in accordance with some of the embodiments of the present disclosure.

FIG. 8 illustrates an example of an in vivo analyte monitoring system 860. For embodiments of the present disclosure this example in vivo analyte monitoring system 860 monitors glucose and, optionally, one or more other analytes.

The in vivo analyte monitoring system 860 comprises a sensor control device 862 (which may be at least a portion of the glucose monitor 324 of FIG. 3) and a reader device 864 (which may be at least a portion of the health monitoring device 320 of FIG. 3) that communicate with each other over a local communication path (or link) 866, which can be wired or wireless, and uni-directional or bi-directional. In embodiments where path 866 is wireless, a near field communication (NFC) protocol, RFID protocol, BLUETOOTH® or BLUETOOTH® Low Energy protocol, WiFi protocol, proprietary protocol, or the like can be used, including those communication protocols in existence as of the date of this filing or their later developed variants.

Reader device 864 (e.g., a dedicated reader, a cellular phone or PDA running an app, or the like) is also capable of wired, wireless, or combined communication with a computer system 868 (which may be at least a portion of the data processing terminal/PC 326 of FIG. 3) over communication path (or link) 870 and with a network 872 (which may be at least a portion of the data network 322 and/or the server/cloud 328 of FIG. 3), such as the internet or the cloud, over communication path (or link) 874. Communication with network 872 can involve communication with trusted computer system 876 within network 872, or though network 872 to computer system 868 via communication link (or path) 878. Communication paths 870, 874, and 878 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 870 and 874 can be the same path. All communications over paths 866, 870, and 874 can be encrypted and sensor control device 862, reader device 864, computer system 868, and trusted computer system 876 can each be configured to encrypt and decrypt those communications sent and received.

Variants of devices 862 and 864, as well as other components of an in vivo-based analyte monitoring system that are suitable for use with the system, device, and method embodiments set forth herein, are described in US Patent Application Publication No. 2011/0213225 (the '225 Publication), which is incorporated by reference herein in its entirety for all purposes.

Sensor control device 862 can include a housing 880 containing in vivo analyte monitoring circuitry and a power source. In this embodiment, the in vivo analyte monitoring circuitry is electrically coupled with an analyte sensor 882 that extends through an adhesive patch 884 and projects away from housing 880. Adhesive patch 884 contains an adhesive layer (not shown) for attachment to a skin surface of the body of the subject. Other forms of body attachment to the body may be used, in addition to or instead of adhesive.

Sensor 882 is adapted to be at least partially inserted into the body of the subject, where it can make fluid contact with that subject's bodily fluid (e.g., subcutaneous (subdermal) fluid, dermal fluid, or blood) and be used, along with the in vivo analyte monitoring circuitry, to measure analyte-related data of the subject. Sensor 882 and any accompanying sensor control electronics can be applied to the body in any desired manner. For example, an insertion device (not shown) can be used to position all or a portion of analyte sensor 882 through an external surface of the subject's skin and into contact with the subject's bodily fluid. In doing so, the insertion device can also position sensor control device 862 with adhesive patch 884 onto the skin. In other embodiments, insertion device can position sensor 882 first, and then accompanying sensor control electronics can be coupled with sensor 882 afterwards, either manually or with the aid of a mechanical device. Examples of insertion devices are described in US Patent Application Publication Nos. 2008/0009692, 2011/0319729, 2015/0018639, 2015/0025345, and 2015/0173661, all which are incorporated by reference herein in their entireties and for all purposes.

After collecting raw data from the subject's body, sensor control device 432 can apply analog signal conditioning to the data and convert the data into a digital form of the conditioned raw data. In some embodiments, this conditioned raw digital data can be encoded for transmission to another device (e.g., reader device 864), which then algorithmically processes that digital raw data into a final form representative of the subject's measured biometric (e.g., a form readily made suitable for display to the subject or readily used in the analysis module 320B of FIG. 3). This algorithmically processed data can then be formatted or graphically processed for digital display to the subject. In other embodiments, sensor control device 862 can algorithmically process the digital raw data into the final form that is representative of the subject's measured biometric (e.g., analyte level) and then encode and wirelessly communicate that data to reader device 864, which in turn can format or graphically process the received data for digital display to the subject. In other embodiments, sensor control device 862 can graphically process the final form of the data such that it is ready for display, and display that data on a display of sensor control device 862 or transmit the data to reader device 864. In some embodiments, the final form of the biometric data (prior to graphic processing) is used by the system (e.g., incorporated into a diabetes monitoring regime) without processing for display to the subject. In some embodiments, sensor control device 862 and reader device 864 transmit the digital raw data to another computer system for algorithmic processing and display.

Reader device 864 can include a display 886 to output information to the subject (e.g., one or more physiological parameter or an output derived therefrom like cHbA1c) and/or to accept an input from the subject, and an optional input component 888 (or more), such as a button, actuator, touch sensitive switch, capacitive switch, pressure sensitive switch, jog wheel or the like, to input data, commands, or otherwise control the operation of reader device 864. In certain embodiments, display 886 and input component 888 may be integrated into a single component, for example, where the display can measure the presence and location of a physical contact touch upon the display, such as a touch screen subject interface (which may be at least a portion of the subject interface 320A of FIG. 3). In certain embodiments, input component 888 of reader device 864 may include a microphone and reader device 864 may include software configured to analyze audio input received from the microphone, such that functions and operation of the reader device 864 may be controlled by voice commands. In certain embodiments, an output component of reader device 864 includes a speaker (not shown) for outputting information as audible signals. Similar voice responsive components such as a speaker, microphone and software routines to generate, process, and store voice driven signals may be included in sensor control device 862.

Reader device 864 can also include one or more data communication ports 890 for wired data communication with external devices such as computer system 868. Example data communication ports 890 include, but are not limited to, USB ports, mini USB ports, USB Type-C ports, USB micro-A and/or micro-B ports, RS-232 ports, Ethernet ports, Firewire ports, or other similar data communication ports configured to connect to the compatible data cables. Reader device 864 may also include an integrated or attachable in vitro glucose meter, including an in vitro test strip port (not shown) to receive an in vitro glucose test strip for performing in vitro blood glucose measurements.

Reader device 864 can display the measured biometric data wirelessly received from sensor control device 862 and can also be configured to output alarms (e.g., a visual alarm on a display, an auditory alarm, or a combination thereof), alert notifications, glucose levels, etc., which may be visual, audible, tactile, or any combination thereof. Further details and other display embodiments can be found in US Patent Application Publication No. 2011/0193704, for example, which is incorporated herein by reference in its entirety for all purposes.

Reader device 864 can function as a data conduit to transfer the measured data from sensor control device 862 to computer system 868 or trusted computer system 876. In certain embodiments, the data received from sensor control device 862 may be stored (permanently or temporarily) in one or more memories of reader device 120 prior to uploading to computer system 868, trusted computer system 876, or network 872.

Computer system 868 may be a personal computer, a server terminal, a laptop computer, a tablet, or other suitable data processing device. Computer system 868 can be (or include) software for data management and analysis and communication with the components in analyte monitoring system 860. Computer system 868 can be used by the subject, a medical professional, or other user to display and/or analyze the biometric data measured by sensor control device 862. In some embodiments, sensor control device 862 can communicate the biometric data directly to computer system 868 without an intermediary such as reader device 864, or indirectly using an internet connection (also optionally without first sending to reader device 864). Operation and use of computer system 438 is further described in the '225 Publication incorporated herein. Analyte monitoring system 430 can also be configured to operate with a data processing module (not shown), also as described in the incorporated '225 Publication.

Trusted computer system 876 can be within the possession of the manufacturer or distributor of sensor control device 862, either physically or virtually through a secured connection, and can be used to perform authentication of sensor control device 862, for secure storage of the subject's biometric data, and/or as a server that serves a data analytics program (e.g., accessible via a web browser) for performing analysis on the subject's measured data.

In vivo analyte monitoring systems can be used in conjunction with or as a portion of an integrated diabetes management system. For example, an integrated diabetes management system may include an in vivo analyte monitoring system and a supplement/medication delivery system, and more specifically, an in vivo glucose monitoring system and an insulin delivery system (e.g., an insulin pump). Integrated diabetes management systems may be closed-loop, open-loop, or a hybrid thereof. Closed-loop systems are in full control of analyte measurement times and supplement/medication dosages and times. Open-loop systems allow a subject to be in full control of analyte measurement times and supplement/medication dosages and times. Hybrid systems can rely primarily on a closed-loop system methodology but allows a subject to intervene.

In vitro analyte monitoring systems contact a bodily fluid outside of the body. In some instances, in vitro analyte monitoring systems include a meter device that has a port for receiving the bodily fluid of the subject (e.g., on an analyte test strip/swab or via collection of the bodily fluid), which can be analyzed to determine the subject's analyte level.

Example Embodiments

Examples of embodiments of the present disclosure include Embodiment A, Embodiment C, Embodiment D, Embodiment E, Embodiment F, Embodiment G, Embodiment H, Embodiment I, and Embodiment J. Combinations of such embodiments are also included as part of the present disclosure.

Embodiment A is a method comprising: providing (or receiving (e.g., from one or more processors)) a plurality of glucose levels over a first time period; providing (or receiving (e.g., from one or more processors)) a first glycated hemoglobin (HbA1c) level corresponding to an end of the first time period; and determining (e.g., calculating) at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of glucose levels and (2) the first HbA1c level.

Embodiment B is a method comprising: measuring a plurality of glucose levels over a first time period; measuring a first glycated hemoglobin (HbA1c) level corresponding to an end of the first time period; and determining (e.g., calculating) at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of glucose levels and (2) the first HbA1c level.

Embodiment A or B may optionally include additional elements, which may include, but are not limited to: Element 1: wherein the first time period is about 300 days or longer and the plurality of glucose levels occur on average about 96 or more times daily; Element 2: the method further comprising measuring a second HbA1c level corresponding to a beginning of the first time period and, optionally, wherein the first time period is about 30 days or longer, and the plurality of glucose levels occur on average about 24 or more times daily; Element 3: wherein at least some of the plurality of glucose levels are measured with an in vivo analyte sensor having a portion positioned to be in contact with a bodily fluid, the in vivo analyte sensor generating signals corresponding to plurality of glucose levels in the bodily fluid; Element 4: Element 3 and wherein the bodily fluid comprises a fluid selected from the group consisting of: blood, dermal fluid, interstitial fluid, or a combination thereof; Element 5: Element 3 and wherein the in vivo analyte sensor is a component of a closed-loop control system or a hybrid closed-loop control system for delivering an insulin dosage; Element 6: wherein at least some of the plurality of glucose levels are measured by a continuous glucose monitoring system; Element 7: wherein at least some of the plurality of glucose levels are input based on a test strip glucose level measurement; Element 8: Element 7 and wherein the test strip glucose level measurement measures the plurality of glucose levels in a fluid selected from the group consisting of: blood, interstitial fluid, subcutaneous fluid, dermal fluid, sweat, tears, saliva, or a combination thereof; Element 9: the method further comprising displaying the at least one physiological parameter; Element 10: the method further comprising calculating an error associated with the at least one physiological parameter; and measuring at least one new glucose level and/or measuring at least one new HbA1c level when the error is at or greater than about 7%; Element 11: the method further comprising calculating a metabolic age based on $k_{age}$ and/or K; Element 12: the method further comprising calculating a personalized-target glucose range based on the at least one physiological parameter; Element 13: the method further comprising calculating a personalized-target average glucose based on the at least one physiological parameter; Element 14: the method further comprising calculating a cHbA1c based on the at least one physiological parameter and a plurality of glucose levels over a second time period following the first time period; Element 15: the method further comprising triaging a subject's treatment based on the at least one physiological parameter; Element 16: the method further comprising adjusting a dosage of diabetes medication based on the at least one physiological parameter; Element 17: the method further comprising adjusting a dosage of glycation medication based on the at least one physiological parameter; Element 18: the method further comprising determining an abnormal or diseased physiological condition of a subject based on the at least one physiological parameter; and Element 19: the method further comprising determining a type of a medication or supplement in a subject's body based on the at least one physiological parameter. Examples of combinations of elements include, but are not limited to, two or more of Elements 11-19 in combination; Elements 6 and 7 in combination, optionally in further combination with Element 8; Element 6 in combination with Element 3, optionally in further combination with one or both of Elements 4-5; Elements 9-10 in combination; Element 9 and/or Element 10 in combination with one or more of Elements 11-19; one or more of Elements 3-8 combination with one or more of Elements 11-19; and Element 1 or Element 2 in combination with one or more of Elements 3-19 including any of the foregoing combinations of Elements 3-19.

Embodiment C is and apparatus comprising: one or more processors; and a memory operatively coupled to the one or more processors storing instructions which, when executed by the one or more processors, causes the one or more processors to: receive a plurality of glucose levels over a first time period; receive a first glycated hemoglobin (HbA1c) level corresponding to an end of the first time period; and determine at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of glucose levels and (2) the first HbA1c level.

Embodiment D is a system comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of glucose levels over a first time period form the analyte sensor; receive a first glycated hemoglobin (HbA1c) level corresponding to an end of the first time period; and determine at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of glucose levels and (2) the first HbA1c level.

Embodiment E is a system comprising: one or more processors; an in vivo analyte sensor having a portion positioned to be in contact with a bodily fluid, the in vivo analyte sensor generating signals corresponding to glucose levels in the bodily fluid; a transmitter coupled to the in vivo analyte sensor and to at least one processor of the one or more processors; and a memory operatively coupled to the one or more processors storing instructions which, when executed by the one or more processors, causes the one or more processors to: receive a plurality of glucose levels over a first time period form the analyte sensor; receive a first glycated hemoglobin (HbA1c) level corresponding to an end of the first time period; and determine at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of glucose levels and (2) the first HbA1c level.

Embodiments C, D, and E may optionally include additional elements, which may include, but are not limited to: Element 1; Element 20: wherein the instructions which, when executed by the one or more processors, causes the one or more processors to further: receive a second HbA1c level corresponding to a beginning of the first time period and, optionally, wherein the first time period is about 30 days or longer and the plurality of glucose levels occur on average about 24 or more times daily; Element 21: configured to receive at least some of the plurality of glucose levels from an in vivo analyte sensor having a portion positioned to be in contact with bodily fluid; Element 22: configured to receive at least some of the plurality of glucose levels from a continuous glucose monitoring system; Element 23: configured to receive at least some of the plurality of glucose levels from a subject based on a test strip glucose level measurement; Element 24: wherein the instructions which, when executed by the one or more processors, causes the one or more processors to further: display the at least one physiological parameter; Element 25: wherein the instructions which, when executed by the one or more processors, causes the one or more processors to further: determine an error associated with the at least one physiological parameter; and request at least one new glucose level and/or request at least one new HbA1c level when the error is at or greater than about 7%; Element 26: wherein the instructions which, when executed by the one or more processors, causes the one or more processors to further: calculate a metabolic age based on $k_{age}$ and/or K and, optionally, output a report that includes the metabolic age; Element 27: wherein the instructions which, when executed by the one or more processors, causes the one or more processors to further: calculate a personalized-target glucose range based on the at least one physiological parameter and, optionally, output a report that includes the personalized-target glucose range; Element 28: wherein the instructions which, when executed by the one or more processors, causes the one or more processors to further: calculate a personalized-target average glucose based on the at least one physiological parameter and, optionally, output a report that includes the personalized-target average glucose; Element 29: wherein the instructions which, when executed by the one or more processors, causes the one or more processors to further: calculate a cHbA1c based on the at least one physiological parameter and a plurality of glucose levels over a second time period following the first time period and, optionally, output a report that includes the cHbA1c; Element 30: wherein the instructions which, when executed by the one or more processors, causes the one or more processors to further: output a triage recommendation for a subject's treatment based on the at least one physiological parameter and, optionally, output a report that includes the triage recommendation; Element 31: wherein the instructions which, when executed by the one or more processors, causes the one or more processors to further: output a dosage of diabetes medication based on the at least one physiological parameter and, optionally, output a report that includes the dosage of diabetes medication; Element 32: wherein the instructions which, when executed by the one or more processors, causes the one or more processors to further: output a dosage of glycation medication based on the at least one physiological parameter and, optionally, output a report that includes the dosage of glycation medication; Element 33: wherein the instructions which, when executed by the one or more processors, causes the one or more processors to further: output an abnormal or diseased physiological condition of a subject based on the at least one physiological parameter and, optionally, output a report that includes the abnormal or diseased physiological condition; and Element 34: wherein the instructions which, when executed by the one or more processors, causes the one or more processors to further: output a type of a medication or supplement in a subject's body based on the at least one physiological parameter and, optionally, output a report that includes the type of the medication or supplement. Examples of combinations of elements include, but are not limited to, two or more of Elements 26-34 in combination; two or more of Elements 21-25 in combination; one or more of Elements 21-25 in combination with one or more of Elements 26-34; Element 1 or Element 20 in combination with one or more of Elements 21-34 including any of the foregoing combinations of Elements 21-34.

Embodiment F is a method comprising: providing (or receiving (e.g., from one or more processors)) at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K) for a first time period based on a plurality of first glucose levels and a first glycated hemoglobin (HbA1c) level corresponding to an end of the first time period and a beginning of a second time period after the first time period; and determining (e.g., calculating) (or adjusting or correcting) (1) a personalized-target glucose range and/or (2) a personalized-target average glucose based on the at least one physiological parameter.

Embodiment G is a method comprising: measuring a plurality of first glucose levels over a first time period; measuring a first glycated hemoglobin (HbA1c) level corresponding to an end of the first time period; determining (e.g., calculating) at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level; and determining (e.g., calculating) (or adjusting or correcting) (1) a personalized-target glucose range and/or (2) a personalized-target average glucose based on the at least one physiological parameter.

Embodiments F and G may optionally include additional elements, which may include, but are not limited to: Element 1; Element 2; Element 3; Element 4; Element 5; Element 6; Element 7; Element 8; Element 35: wherein the at least one physiological parameter comprises K, and the personalized-target glucose range has an upper limit according to Equation 10±7% and/or Equation 12±7%; Element 36: wherein the at least one physiological parameter comprises $k_{gly}$, and wherein the personalized-target glucose range has a lower limit of the personalized-target glucose range according to Equation 9±7% and/or Equation 11±7%; Element 37: wherein the at least one physiological parameter comprises K, and wherein the personalized-target average glucose (GT) equals AT/(K(1−AT)) where AT is a target HbA1c level; Element 38: wherein determining (1) the personalized-target glucose range and/or (2) the personalized-target average glucose is further based on at least one subject-specific parameter selected from the group consisting of a family history of a medical condition, a known medical condition, an age, a race, a gender, a geographic location, a diabetes type, a duration of diabetes diagnosis, and a combination thereof; Element 39: the method further comprising calculating an error associated with the at least one physiological parameter; and measuring at least one new glucose level and/or measuring at least one new HbA1c level when the error is at or greater than about 7%; Element 40: the method further comprising treating a subject based on (1) the personalized-target glucose range and/or (2) the personalized-target average glucose; Element 41: Element 40 and wherein treating the subject comprises administering and/or adjusting: an insulin dosage, a glycation-medication dosage, an exercise regime, a meal intake, or a combination thereof; Element 42: the method further comprising displaying (1)

the personalized-target glucose range and/or (2) the personalized-target average glucose; Element 43: the method further comprising measuring a glucose level of a subject after determining the personalized-target glucose range; and displaying an alarm when the glucose level is outside the personalized-target glucose range; Element 44: the method further comprising calculating a metabolic age based on $k_{age}$ and/or K; Element 45: the method further comprising measuring a plurality of second glucose levels for a second time period after the first time period; and determining a calculated glycated hemoglobin (cHbA1c) level based on (1) the $k_{gly}$, (2) the $k_{age}$, (3) the plurality of second glucose levels for the second time period, and (4) the first HbA1c level; and Element 46: the method further comprising measuring a second HbA1c level for an end of a second time period following the first time period; calculating at least one second physiological parameter corresponding to the at least one first physiological parameter; and identifying (1) a presence of an abnormal or diseased physiological condition and/or (2) an indicator of doping based on a comparison of the at least one first physiological parameter and the at least one second physiological parameter. Examples of combinations of elements include, but are not limited to, two or more of Elements 35-37 in combination; two or more of Elements 38-43 in combination; one or more of Elements 35-37 in combination with one or more of Elements 38-43; two or more of Elements 44-46 in combination; one or more of Elements 44-46 in combination with one or more of Elements 35-43; and one or more of Elements 3-8 in combination with one or more of Elements 35-46 including any of the foregoing combinations of Elements 35-46; and Element 1 or Element 2 in combination with one or more of Elements 3-8 and 35-46 including any of the foregoing combinations of Elements 3-8 and 35-46.

Embodiment H is a device comprising: a memory operatively coupled to one or more processors storing instructions which, when executed by the one or more processors, causes the one or more processors to: receive a plurality of first glucose levels in the bodily fluid over a first time period from the analyte sensor; receive a first glycated hemoglobin (HbA1c) level corresponding to an end of the first time period; determine at least one physiological parameter selected from the group consisting of: a red blood cell glycation rate constant ($k_{gly}$), a red blood cell generation rate constant ($k_{gen}$), a red blood cell elimination rate constant ($k_{age}$), and an apparent glycation constant (K), based on (1) the plurality of first glucose levels and (2) the first HbA1c level; and determine (1) a personalized-target glucose range and/or (2) a personalized-target average glucose based on the at least one physiological parameter.

Embodiment I is a system comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of first glucose levels in the bodily fluid over a first time period from the analyte sensor; receive a first glycated hemoglobin (HbA1c) level corresponding to an end of the first time period; determine at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level; and determine (1) a personalized-target glucose range and/or (2) a personalized-target average glucose based on the at least one physiological parameter.

Embodiment J is a system comprising: one or more processors; an in vivo analyte sensor having a portion positioned to be in contact with a bodily fluid, the in vivo analyte sensor generating signals corresponding to glucose levels in the bodily fluid; a transmitter coupled to the in vivo analyte sensor and to at least one processor of the one or more processors; and a memory operatively coupled to the one or more processors storing instructions which, when executed by the one or more processors, causes the one or more processors to: receive a plurality of first glucose levels in the bodily fluid over a first time period from the analyte sensor; receive a first glycated hemoglobin (HbA1c) level corresponding to an end of the first time period; determine at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level; and determine (1) a personalized-target glucose range and/or (2) a personalized-target average glucose based on the at least one physiological parameter.

Embodiments H, I, and J may optionally include additional elements, which may include, but are not limited to: Element 1; Element 20; Element 35; Element 36; Element 37; Element 47: the system further comprising a display, wherein the instructions which, when executed by the one or more processors, causes the one or more processors to further: display (1) the personalized-target glucose range and/or (2) the personalized-target average glucose; Element 48: Element 47 and wherein the instructions which, when executed by the one or more processors, causes the one or more processors to further: receive a plurality of second glucose levels in the bodily fluid over a second time period after the first time period from the analyte sensor; and display an alarm when a glucose level from the plurality of second glucose levels is outside the personalized-target glucose range; Element 49: wherein the instructions which, when executed by the one or more processors, causes the one or more processors to further: determine an error associated with the at least one physiological parameter; and output a request for at least one new glucose level and/or at least one new HbA1c level when the error is at or greater than about 7%; Element 50: wherein the instructions which, when executed by the one or more processors, causes the one or more processors to further: determine a metabolic age based on $k_{age}$ and/or K; Element 51: wherein the instructions which, when executed by the one or more processors, causes the one or more processors to further: receive a plurality of second glucose levels for a second time period after the first time period from the analyte sensor; and determine a calculated glycated hemoglobin (cHbA1c) level based on (1) the $k_{gly}$, (2) the $k_{age}$, (3) the plurality of second glucose levels for the second time period, and (4) the first HbA1c level; Element 52: wherein the instructions which, when executed by the one or more processors, causes the one or more processors to further: receive a second HbA1c level for an end of a second time period following the first time period; determine at least one second physiological parameter corresponding to the at least one first physiological parameter; and identify (1) a presence of an abnormal or diseased physiological condition and/or (2) an indicator of doping based on a comparison of the at least one first physiological parameter and the at least one second physiological parameter; and Element 53: wherein the instructions, when executed, cause the one or more processors to: determine an insulin dosage based on (1) the personalized-target glucose range and/or (2) the personalized-target average glucose; and transmit the insulin dosage to an insulin pump system. Examples of combinations of elements include, but are not limited to, two or more of Elements 35-37 in combination; two or more of Elements 47-53 in combination; one or more of Elements 35-37 in combination with one or more of Elements 47-53; and Element 1 or Element 20 in combination with one or more of Elements 35-37 and 47-53 including any of the foregoing combinations of Elements 35-37 and 47-53.

Embodiment K is a method comprising: providing (or receiving (e.g., from one or more processors)) a red blood cell glycation rate constant ($k_{gly}$) and a red blood cell elimination constant ($k_{age}$) for a first time period based on a plurality of first glucose levels and a first glycated hemoglobin (HbA1c) level corresponding to an end of the first time period and a beginning of a second time period after the first time period; measuring a plurality of second glucose levels for the second time period; and determining (e.g., calculating) a calculated glycated hemoglobin (cHbA1c) level based on (1) the $k_{gly}$, (2) the $k_{age}$, (3) the plurality of second glucose levels for the second time period, and (4) the first HbA1c level.

Embodiment L is a method comprising: measuring a plurality of first glucose levels over the first time period; measuring a first glycated hemoglobin (HbA1c) level corresponding to an end of the first time period and a beginning of a second time period after the first time period; determining (e.g., calculating) a red blood cell glycation rate constant ($k_{gly}$) and a red blood cell elimination constant ($k_{age}$) for a first time period based on the plurality of first glucose levels and the first HbA1c level; measuring a plurality of second glucose levels for the second time period after the first time period; and determining (e.g., calculating) a calculated glycated hemoglobin (cHbA1c) level based on (1) the $k_{gly}$, (2) the $k_{age}$, (3) the plurality of second glucose levels for the second time period, and (4) the first HbA1c level.

Embodiment K and L may optionally include additional elements, which may include, but are not limited to: Element 1; Element 2; Element 3; Element 4; Element 5; Element 6; Element 7; Element 8; Element 54: wherein the cHbA1c is HbA1c$_z$ of Equation 8; Element 55: the method further comprising calculating an error associated with at least one of $k_{gly}$ and $k_{age}$; and measuring at least one new glucose level and/or measuring at least one new HbA1c level when the error is at or greater than about 7%; Element 56: the method further comprising treating a subject based on the cHbA1c; Element 57: Element 56 and wherein treating the subject comprises administering and/or adjusting: an insulin dosage, a glycation-medication dosage, an exercise regime, a meal intake, or a combination thereof; Element 58: the method further comprising displaying the cHbA1c, optionally, as a portion of a report; and Element 59: wherein the second time period is about 14 days or longer, and the plurality of second glucose levels occur on average about 96 or more times daily. Examples of combinations of elements include, but are not limited to, two or more of Elements 54-59 in combination; one or more of Elements 3-8 in combination with one or more of Elements 54-59 including any of the foregoing combinations of Elements 54-59; and Element 1 or Element 2 in combination with one or more of Elements 3-8 and 54-59 including any of the foregoing combinations of Elements 3-8 and 54-59.

Embodiment M is an apparatus comprising: one or more processors; and a memory operatively coupled to the one or more processors storing instructions which, when executed by the one or more processors, causes the one or more processors to: receive a plurality of first glucose levels over a first time period; receive a first glycated hemoglobin (HbA1c) level corresponding to an end of the first time period and a beginning of a second time period after the first time period; determine a red blood cell glycation rate constant ($k_{gly}$) and a red blood cell elimination constant ($k_{age}$) for the first time period based on the plurality of first glucose levels and the first HbA1c level; receive a plurality of second glucose levels for the second time period; and determine a calculated glycated hemoglobin (cHbA1c) level based on (1) the $k_{gly}$, (2) the $k_{age}$, (3) the plurality of second glucose levels for the second time period, and (4) the first HbA1c level.

Embodiment N is a system comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of first glucose levels over a first time period from the analyte sensor; receive a first glycated hemoglobin (HbA1c) level corresponding to an end of the first time period and a beginning of a second time period after the first time period; determine a red blood cell glycation rate constant ($k_{gly}$) and a red blood cell elimination constant ($k_{age}$) for the first time period based on the plurality of first glucose levels and the first HbA1c level; receive a plurality of second glucose levels for the second time period from the analyte sensor; and determine a calculated glycated hemoglobin (cHbA1c) level based on (1) the $k_{gly}$, (2) the $k_{age}$, (3) the plurality of second glucose levels for the second time period, and (4) the first HbA1c level.

Embodiment O is a system comprising: one or more processors; an in vivo analyte sensor having a portion positioned to be in contact with a bodily fluid, the in vivo analyte sensor generating signals corresponding to glucose levels in the bodily fluid; a transmitter coupled to the in vivo analyte sensor and to at least one processor of the one or more processors; and a memory operatively coupled to the one or more processors storing instructions which, when executed by the one or more processors, causes the one or more processors to: receive a plurality of first glucose levels over a first time period from the analyte sensor; receive a first glycated hemoglobin (HbA1c) level corresponding to an end of the first time period and a beginning of a second time period after the first time period; determine a red blood cell glycation rate constant ($k_{gly}$) and a red blood cell elimination constant ($k_{age}$) for the first time period based on the plurality of first glucose levels and the first HbA1c level; receive a plurality of second glucose levels for the second time period from the analyte sensor; and determine a calculated glycated hemoglobin (cHbA1c) level based on (1) the $k_{gly}$, (2) the $k_{age}$, (3) the plurality of second glucose levels for the second time period, and (4) the first HbA1c level.

Embodiments M, N, and O may optionally include additional elements, which may include, but are not limited to: Element 1; Element 20; Element 54; Element 60: wherein the instructions, when executed, cause the one or more processors to: determine an error associated with at least one of $k_{gly}$ and $k_{age}$; and request at least one new glucose level and/or request at least one new HbA1c level when the error is at or greater than about 7%; Element 61: wherein the instructions, when executed, cause the one or more processors to: determine a treatment based on the cHbA1c; Element 62: Element 61 and wherein the treatment comprises determining an insulin dosage and/or determining a glycation-medication dosage; and Element 63: wherein the instructions, when executed, cause the one or more processors to: determine an insulin dosage based on the cHbA1c; and transmit the insulin dosage to an insulin pump system. Examples of combinations can include, but are not limited to; two or more of Elements 54 and 60-63 in combination; and Element 1 or Element 20 in combination with one or more of Elements 54 and 60-63.

Embodiment P is a method comprising: providing (or receiving (e.g., from one or more processors)) at least one first physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K) for a first time period based on a plurality of first glucose levels over the first time period and a first glycated hemoglobin (HbA1c) level corresponding to an end of the first time period; measuring a plurality of second glucose levels for a second time period after the first time period; measuring a second glycated hemoglobin (HbA1c) level for an end of the second time period; calculating at least one second physiological parameter corresponding to the at least one first physiological parameter; and identifying (1) a presence of an abnormal or diseased physiological condition and/or (2) an indicator of doping based on a comparison of the at least one first physiological parameter and the at least one second physiological parameter.

Embodiment Q is a method comprising: measuring a plurality of first glucose levels over a first time period; measuring a first glycated hemoglobin (HbA1c) level corresponding to an end of the first time period and a beginning of a second time period after the first time period; determining (e.g., calculating) at least one first physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K) for a first time period based on the plurality of first glucose levels and the first HbA1c level; measuring a plurality of second glucose levels for a second time period; measuring a second HbA1c level for an end of the second time period; calculating at least one second physiological parameter corresponding to the at least one first physiological parameter; and identifying (1) a presence of an abnormal or diseased physiological condition and/or (2) an indicator of a doping supplement or medication based on a comparison of the at least one first physiological parameter and the at least one second physiological parameter.

Embodiments P and Q may optionally include additional elements, which may include, but are not limited to: Element 1; Element 2; Element 3; Element 4; Element 5; Element 6; Element 7; Element 8; Element 64: wherein the at least one first physiological parameter and the at least one second physiological parameter both comprise $k_{gly}$; and the abnormal or diseased physiological condition relates to a subject's metabolism; Element 65: wherein the at least one first physiological parameter and the at least one second physiological parameter both comprise $k_{age}$; and the abnormal or diseased physiological condition relates to a subject's immune system; Element 66: wherein the at least one first physiological parameter and the at least one second physiological parameter both comprise $k_{age}$; and the abnormal or diseased physiological condition relates to a subject's oxygen sensing mechanism; Element 67: wherein the at least one first physiological parameter and the at least one second physiological parameter both comprise $k_{age}$; and the abnormal or diseased physiological condition relates to a subject's bone marrow; Element 68: the method further comprising treating the abnormal or diseased physiological condition; Element 69: method further comprising monitoring progress and/or status of the abnormal or diseased physiological condition over a subsequent time period using newly calculated physiological parameters; Element 70: wherein the at least one first physiological parameter and the at least one second physiological parameter both comprise $k_{age}$; and the doping supplement or medication is human growth hormone; Element 71: wherein the at least one first physiological parameter and the at least one second physiological parameter both comprise $k_{gly}$; and the doping supplement or medication is designed to increase metabolic levels; and Element 72: displaying an output related to (1) the presence of an abnormal or diseased physiological condition and/or (2) the indicator of a doping supplement or medication. Examples of combinations can include, but are not limited to, Elements 68 and 69 in combination; Element 68 and/or Element 69 in combination with one of Elements 64-67; Element 71 in combination with one of Elements 70-71; one or more of Elements 3-8 in combination with any of the foregoing; Element 1 or 2 in combination with any of the foregoing; Element 72 in combination with any of the foregoing; and Element 72 in combination with one of Elements 54-59.

Embodiment R is an apparatus comprising: one or more processors; and a memory operatively coupled to the one or more processors storing instructions which, when executed by the one or more processors, causes the one or more processors to: receive a plurality of first glucose levels over a first time period; receive a first glycated hemoglobin (HbA1c) level corresponding to an end of the first time period and a beginning of a second time period after the first time period; determine at least one first physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K) for a first time period based on the plurality of first glucose levels and the first HbA1c level; receive a plurality of second glucose levels for the second time period; receive a second HbA1c level for an end of the second time period; calculate at least one second physiological parameter corresponding to the at least one first physiological parameter; and identify (1) a presence of an abnormal or diseased physiological condition and/or (2) an indicator of a doping supplement or medication based on a comparison of the at least one first physiological parameter and the at least one second physiological parameter.

Embodiment 5 is a system comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of first glucose levels over a first time period; receive a first glycated hemoglobin (HbA1c) level corresponding to an end of the first time period and a beginning of a second time period after the first time period; determine at least one first physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K) for a first time period based on the plurality of first glucose levels and the first HbA1c level; receive a plurality of second glucose levels for the second time period; receive a second HbA1c level for an end of the second time period; calculate at least one second physiological parameter corresponding to the at least one first physiological parameter; and identify (1) a presence of an abnormal or diseased physiological condition and/or (2) an indicator of a doping supplement or medication based on a comparison of the at least one first physiological parameter and the at least one second physiological parameter.

Embodiment T is a system comprising: one or more processors; an in vivo analyte sensor having a portion positioned to be in contact with a bodily fluid, the in vivo analyte sensor generating signals corresponding to glucose levels in the bodily fluid; a transmitter coupled to the in vivo analyte sensor and to at least one processor of the one or more processors; and a memory operatively coupled to the one or more processors storing instructions which, when executed by the one or more processors, causes the one or more processors to: receive a plurality of first glucose levels over a first time period; receive a first glycated hemoglobin (HbA1c) level corresponding to an end of the first time period and a beginning of a second time period after the first time period; determine at least one first physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K) for a first time period based on the plurality of first glucose levels and the first HbA1c level; receive a plurality of second glucose levels for the second time period; receive a second HbA1c level for an end of the second time period; calculate at least one second physiological parameter corresponding to the at least one first physiological parameter; and identify (1) a presence of an abnormal or diseased physiological condition and/or (2) an indicator of a doping supplement or medication based on a comparison of the at least one first physiological parameter and the at least one second physiological parameter.

Embodiments R, S, and T may optionally also comprise a display, wherein the instructions which, when executed by the one or more processors, causes the one or more processors to further: display an output related to (1) the presence of an abnormal or diseased physiological condition and/or (2) the indicator of a doping supplement or medication.

Embodiment U is a method comprising: identifying a subject with a red blood cell generation rate constant ($k_{gen}$) and/or a red blood cell elimination constant ($k_{age}$) based on (1) a plurality of glucose levels over a first time period and (2) a first HbA1c level at an end of the first time period; and treating a subject with a closed-loop control system or a hybrid closed-loop control system for delivering an insulin dosage based on when $k_{gly}$ is $6.4*10^{-6}$ dL*mg$^{-1}$*day$^{-1}$ or less and/or K is $5.0*10^{-4}$ dL/mg or greater.

Embodiment V is a method comprising: measuring a plurality of glucose levels for a first time period; measuring a first glycated hemoglobin (HbA1c) level corresponding to an end of the first time period; determining (e.g., calculating) at least one physiological parameter corresponding to a first time period selected from the group consisting of: a red blood cell glycation rate constant ($k_{gly}$) and an apparent glycation constant (K), based on (1) the plurality of glucose levels and (2) the first HbA1c level; and treating a subject with a closed-loop control system or a hybrid closed-loop control system for delivering an insulin dosage based on when $k_{gly}$ is $6.4*10^{-6}$ dL*mg$^{-1}$*day$^{-1}$ or less and/or K is $5.0*10^{-4}$ dL/mg or greater.

Embodiments U and V may optionally include one or more elements that include, but are not limited to, Element 1; Element 2; Element 3; Element 4; Element 5; Element 6; Element 7; and Element 8. Example combinations include, but are not limited to; two or more of Elements 3-8 in combination and Element 1 or Element 2 in combination with one or more of Elements 3-8.

Embodiment W is an apparatus comprising: one or more processors; and a memory operatively coupled to the one or more processors storing instructions which, when executed by the one or more processors, causes the one or more processors to: receive a plurality of glucose levels for a first time period; receive a first glycated hemoglobin (HbA1c) level corresponding to an end of the first time period; determine at least one physiological parameter corresponding to a first time period selected from the group consisting of: a red blood cell glycation rate constant ($k_{gly}$) and an apparent glycation constant (K), based on (1) the plurality of glucose levels and (2) the first HbA1c level; and identify a subject for treatment with a closed-loop control system or a hybrid closed-loop control system for delivering an insulin dosage based on when $k_{gly}$ is $6.4*10^{-6}$ dL*mg$^{-1}$*day$^{-1}$ or less and/or K is $5.0*10^{-4}$ dL/mg or greater.

Embodiment X is a system comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of glucose levels for a first time period; receive a first glycated hemoglobin (HbA1c) level corresponding to an end of the first time period; determine at least one physiological parameter corresponding to a first time period selected from the group consisting of: a red blood cell glycation rate constant ($k_{gly}$) and an apparent glycation constant (K), based on (1) the plurality of glucose levels and (2) the first HbA1c level; and identify a subject for treatment with a closed-loop control system or a hybrid closed-loop control system for delivering an insulin dosage based on when $k_{gly}$ is $6.4*10^{-6}$ dL*mg$^{-1}$*day$^{-1}$ or less and/or K is $5.0*10^{-4}$ dL/mg or greater.

Embodiment Y is a system comprising: one or more processors; an in vivo analyte sensor having a portion positioned to be in contact with a bodily fluid, the in vivo analyte sensor generating signals corresponding to glucose levels in the bodily fluid; a transmitter coupled to the in vivo analyte sensor and to at least one processor of the one or more processors; and a memory operatively coupled to the one or more processors storing instructions which, when executed by the one or more processors, causes the one or more processors to: receive a plurality of glucose levels for a first time period; receive a first glycated hemoglobin (HbA1c) level corresponding to an end of the first time period; determine at least one physiological parameter corresponding to a first time period selected from the group consisting of: a red blood cell glycation rate constant ($k_{gly}$) and an apparent glycation constant (K), based on (1) the plurality of glucose levels and (2) the first HbA1c level; and identify a subject for treatment with a closed-loop control system or a hybrid closed-loop control system for delivering an insulin dosage based on when $k_{gly}$ is $6.4*10^{-6}$ dL*mg$^{-1}$*day$^{-1}$ or less and/or K is $5.0*10^{-4}$ dL/mg or greater.

Embodiment Z is a method for determining a glucose level target comprising: receiving a plurality of first glucose levels over a first time period (e.g., from one or more processors); receiving a first glycated hemoglobin (HbA1c) level corresponding to an end of the first time period (e.g., from one or more processors); determining at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level; and adjusting a glucose level target based on the at least one physiological parameter.

Embodiment Z may optionally include one or more elements that include, but are not limited to, Element 1; Element 2; Element 3; Element 4; Element 5; Element 6; Element 7; Element 8; Element 60: wherein the glucose level target is one or more value selected from the group consisting of a personalized lower glucose limit, a personalized upper glucose limit, and a personalized-target glucose average; Element 61: wherein the at least one physiological parameter comprises K, and the glucose level target comprises the personalized upper glucose limit equals 0.087/K±7%; Element 62: wherein the at least one physiological parameter comprises $k_{gly}$, and the glucose level target comprises the personalized lower glucose limit equals 3.35× $10^{-4}/k_{gly}$±7%; Element 63: wherein the at least one physiological parameter comprises K, and the glucose level target comprises the personalized-target average glucose (GT) equals AT/(K(1−AT) where AT is a target HbA1c level; Element 64: the method further comprising receiving a second HbA1c corresponding to a beginning of the first time period (e.g., from one or more processors), wherein determination of the at least one physiological parameter is further based on (3) the second HbA1c; Element 65: the method further comprising calculating an error associated with the at least one physiological parameter; and receiving at least one new glucose level and/or receiving at least one new HbA1c level (e.g., from one or more processors) when the error is at or greater than about 7%; Element 66: the method further comprising treating a subject based on the glucose level target; Element 67: Element 66 and wherein treating the subject comprises administering and/or adjusting: an insulin dosage, a glycation-medication dosage, an exercise regime, a meal intake, or a combination thereof; Element 68: the method further comprising displaying the glucose level target; Element 69: the method further comprising receiving a glucose level of a subject (e.g., from one or more processors) after adjusting the glucose level target; and displaying an alarm when the glucose level is outside the glucose level target; Element 70: the method further comprising calculating a metabolic age based on $k_{age}$ and/or K; Element 71: the method further comprising receiving a plurality of second glucose levels for a second time period after the first time period (e.g., from one or more processors); and determining a calculated glycated hemoglobin (cHbA1c) level based on (1) the $k_{gly}$, (2) the $k_{age}$, (3) the plurality of second glucose levels for the second time period, and (4) the first HbA1c level; and Element 72: the method further comprising receiving a second HbA1c level for an end of a second time period following the first time period (e.g., from one or more processors); calculating at least one second physiological parameter corresponding to the at least one first physiological parameter; and identifying (1) a presence of an abnormal or diseased physiological condition and/or (2) an indicator of doping based on a comparison of the at least one first physiological parameter and the at least one second physiological parameter. Examples of combinations of elements may include, but are not limited to, Element 61 and 62 in combination; two or more of Elements 60-63 in combination; two or more of Elements 65-72 in combination; one or more of Elements 60-63 in combination with one or more of Elements 65-72; Element 64 in combination with any of the foregoing; Element 64 in combination with one or more of Elements 60-63 and 65-72; one or more of Elements 3-8 in combination with one or more of Elements 60-72 including any of the foregoing combinations of Elements 60-72; and Element 1 or Element 2 in combination with one or more of Elements 3-8 and 60-72.

Embodiment AA is a system for determining a glucose level target comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of first glucose levels in the bodily fluid over a first time period from the analyte sensor; receive a first glycated hemoglobin (HbA1c) level corresponding to an end of the first time period; determine at least one physiological parameter selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level; and adjust a glucose level target based on the at least one physiological parameter.

Embodiment AA may optionally include one or more elements that include, but are not limited to, Element 1; Element 3; Element 4; Element 5; Element 6; Element 7; Element 8; Element 20; Element 60; Element 61; Element 62; Element 63; Element 73: the system further comprising a display, wherein the instructions which, when executed by the one or more processors, causes the one or more processors to further: display the glucose level target; Element 74: Element 73 and wherein the instructions which, when executed by the one or more processors, causes the one or more processors to further: receive a plurality of second glucose levels in the bodily fluid over a second time period after the first time period from the analyte sensor; and display an alarm when a glucose level from the plurality of second glucose levels is outside the glucose level target; Element 75: wherein the instructions which, when executed by the one or more processors, causes the one or more processors to further: determine an error associated with the at least one physiological parameter; and output a request for at least one new glucose level and/or at least one new HbA1c level when the error is at or greater than about 7%; Element 76: wherein the instructions which, when executed by the one or more processors, causes the one or more processors to further: determine a metabolic age based on $k_{age}$ and/or K; Element 77: wherein the instructions which, when executed by the one or more processors, causes the one or more processors to further: receive a plurality of second glucose levels for a second time period after the first time period from the analyte sensor; and determine a calculated glycated hemoglobin (cHbA1c) level based on (1) the $k_{gly}$, (2) the $k_{age}$, (3) the plurality of second glucose levels for the second time period, and (4) the first HbA1c level; Element 78: wherein the instructions which, when executed by the one or more processors, causes the one or more processors to further: receive a second HbA1c level for an end of a second time period following the first time period; determine at least one second physiological parameter corresponding to the at least one first physiological parameter; and identify (1) a presence of an abnormal or diseased physiological condition and/or (2) an indicator of doping based on a comparison of the at least one first physiological parameter and the at least one second physiological parameter; Element 79: wherein the instructions, when executed, cause the one or more processors to: determine an insulin dosage based on the glucose level target; and transmit the insulin dosage to an insulin pump system. Examples of combinations include, but are not limited to, Element 61 and 62 in combination; two or more of Elements 60-63 in combination; two or more of Elements 73-79 in combination; one or more of Elements 60-63 in combination with one or more of Elements 73-79; one or more of Elements 3-8 in combination with one or more of Elements 73-79 including any of the foregoing combinations of Elements 73-79; and Element 1 or Element 20 in combination with one or more of Elements 3-8 and 73-79.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To facilitate a better understanding of the embodiments of the present invention, the following examples of preferred or representative embodiments are given. In no way should the following examples be read to limit, or to define, the scope of the invention.

EXAMPLES

Data from 148 type 2 and 139 type 1 subjects enrolled in two previous clinical studies having six months of continuous glucose monitoring were analyzed. Only 90 subjects had sufficient data to meet the kinetic model assumptions described above having data with no continuous glucose data gap 12 hours or longer. Study participants had three HbA1c measurements, on days 1, 100 (±5 days), and 200 (±5 days), as well as frequent subcutaneous glucose monitoring throughout the analysis time period, which allowed for analysis of two independent data sections (days 1-100 and days 101-200) per participant.

The first data section (days 1-100) was used to numerically estimate individual $k_{gly}$ and $k_{age}$, which allows prospective calculation of ending cHbA1c of the second data section (days 101-200). This ending cHbA1c can be compared with the observed ending HbA1c to validate the kinetic model described herein. For comparison, an estimated HbA1c for the second data section was calculated based on (1) 14-day mean and (2) 14-day weighted average glucose converted by the accepted regression model from the A1c-Derived Average Glucose (ADAG) study, which both assume $k_{gly}$ is a constant, which as discussed previously is the currently accepted method of relating HbA1c to glucose measurements.

Figure 9A:
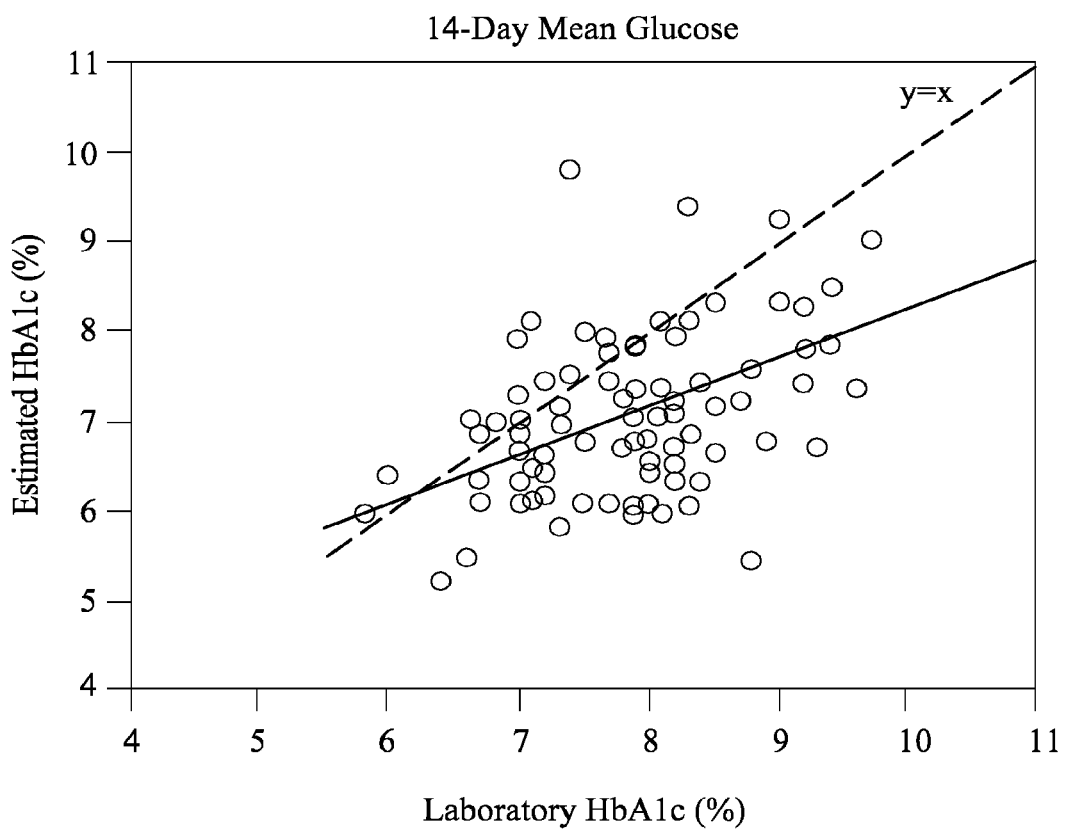
FIGS. 9A-9C illustrate a comparison between the laboratory HbA1c levels at day 200 (±5 days) relative to the estimated HbA1c (eHbA1c) values for two different models (5A and 5B) and calculated HbA1c (cHbA1c) values for the kinetic model of the present disclosure (5C).
Figure 9B:
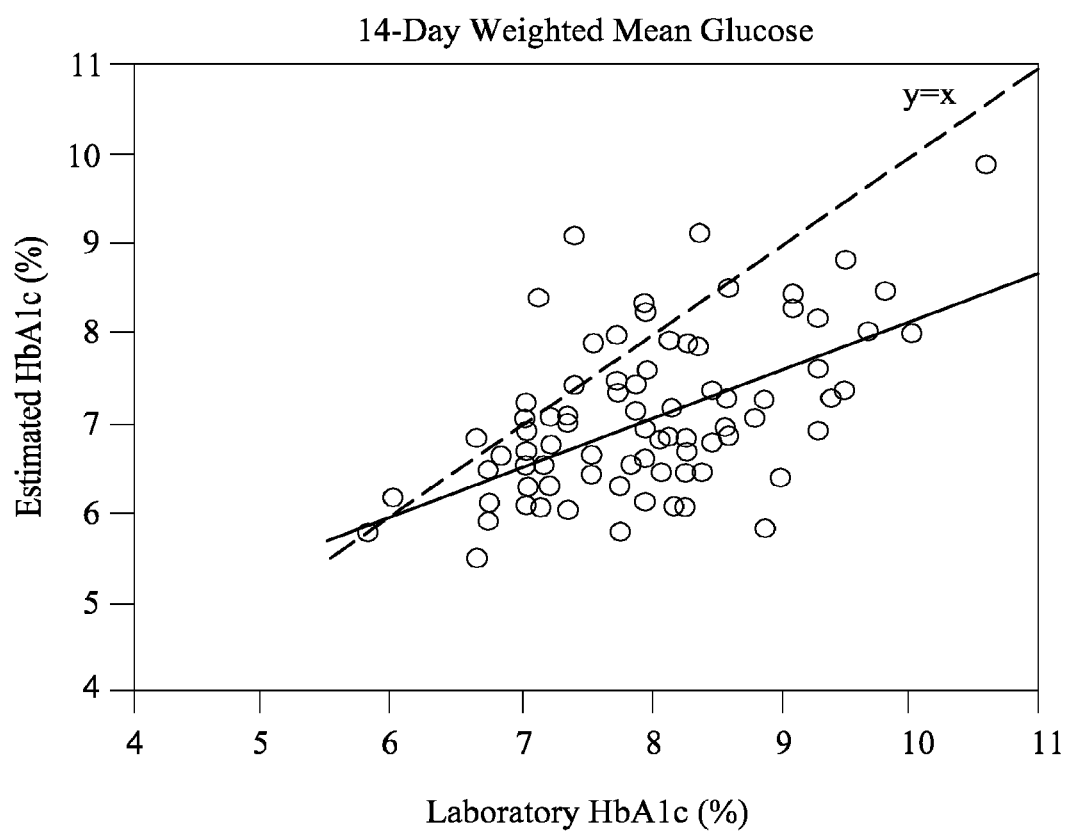
Figure 9C:
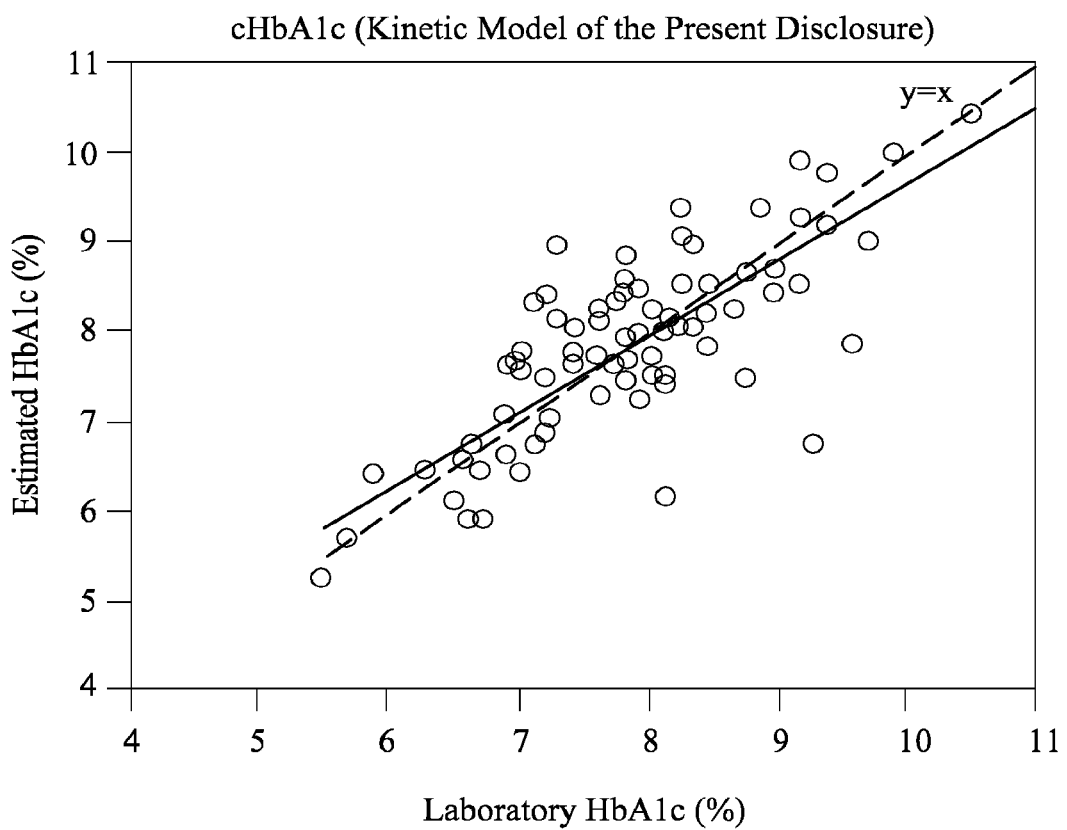

FIGS. 9A-C illustrate a comparison between the laboratory HbA1c levels at day 200 (±5 days) relative to the estimated HbA1c values, where the eHbA1c values in the 5A plot are calculated using the 14-day mean model, the eHbA1c values in the 5B plot are calculated using the 14-day weighted average model, and the cHbA1c values in the 5C plot are calculated using the kinetic model described herein (Equation 8). The solid line in all graphs illustrates the linear regression of the comparative HbA1c values for the corresponding models. The dashed line is a one-to-one line, where the closer the solid line linear regression is thereto, the better the model. Clearly, the kinetic model described herein models the data better, which illustrates that $k_{age}$ and $k_{gly}$ are individualized, which is a novel way to approach correlating HbA1c to glucose measurements.

Figure 10:
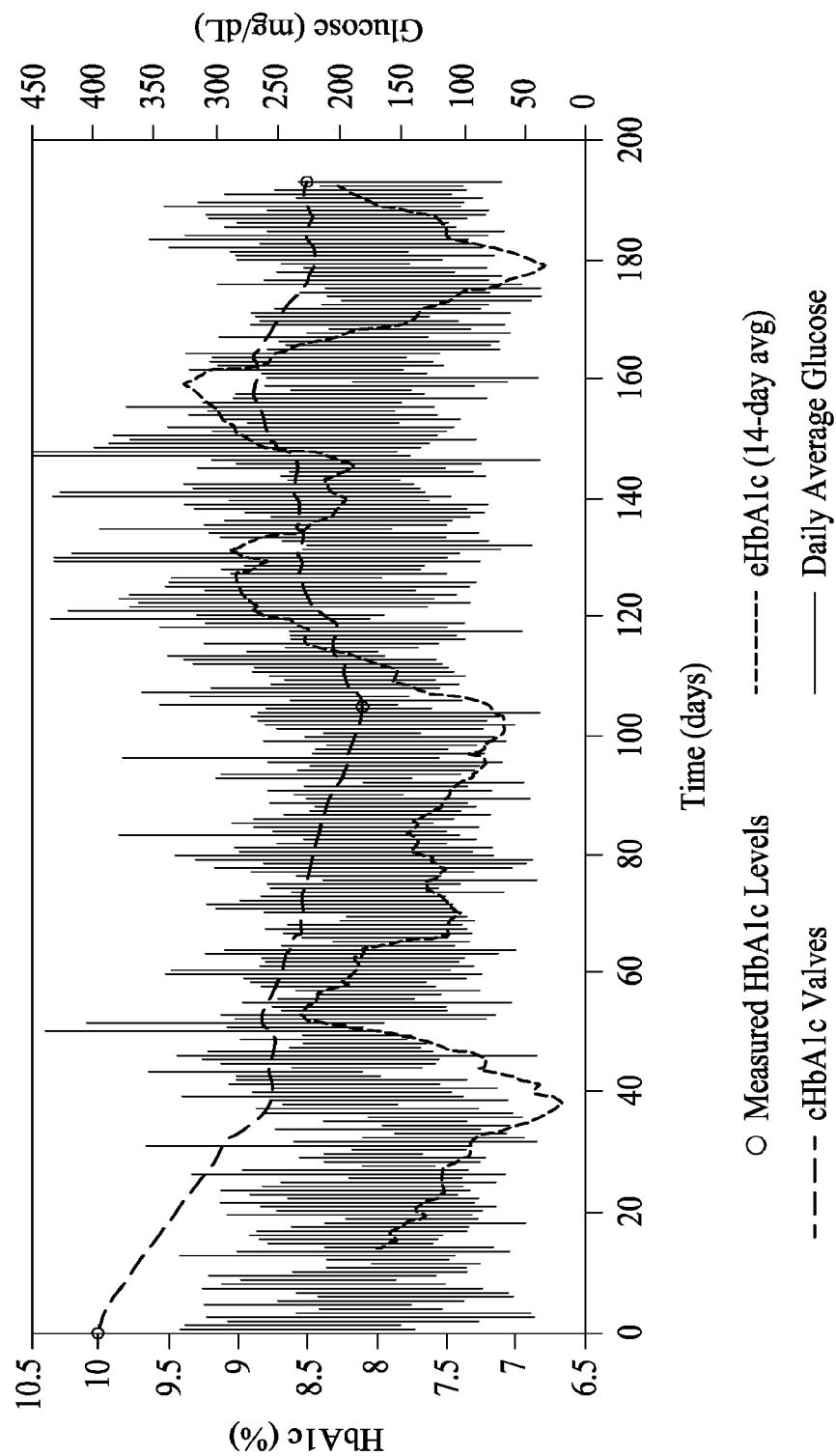
FIG. 10 illustrates an example study subject's data with the glucose trace (solid line), laboratory HbA1c readings (open circles), cHbA1c model values (long dashed line), and 14-day eHbA1c model values (dotted line).

FIG. 10 illustrates an example study subject's data with the glucose trace (solid line), laboratory HbA1c readings (open circles), cHbA1c model values (long dashed line), and 14-day eHbA1c model values (dotted line). The cHbA1c model values in FIG. 10 were calculated using the physiological parameters ($k_{age}$ and $k_{gly}$). The physiological parameters were calculated based on the first two laboratory HbA1c readings and glucose levels measured between the first two laboratory HbA1c readings. The 14-day eHbA1c values are glucose level 14-day running averages during the study.

The FIG. 10 example shows the dynamic nature of the glucose-to-cHbA1c and glucose-to-eHbA1c relationships. Additional examples were determined for type 1 and type 2 diabetes study participants across a range of prediction deviations: 25th, 50th and 75th percentiles for the cHbA1c method. In these examples, the disagreement between the cHbA1c from the 14-day average glucose is illustrated, indicating the exaggerated amplitude of variation inherent in the simple 14-day method.

Figure 11:
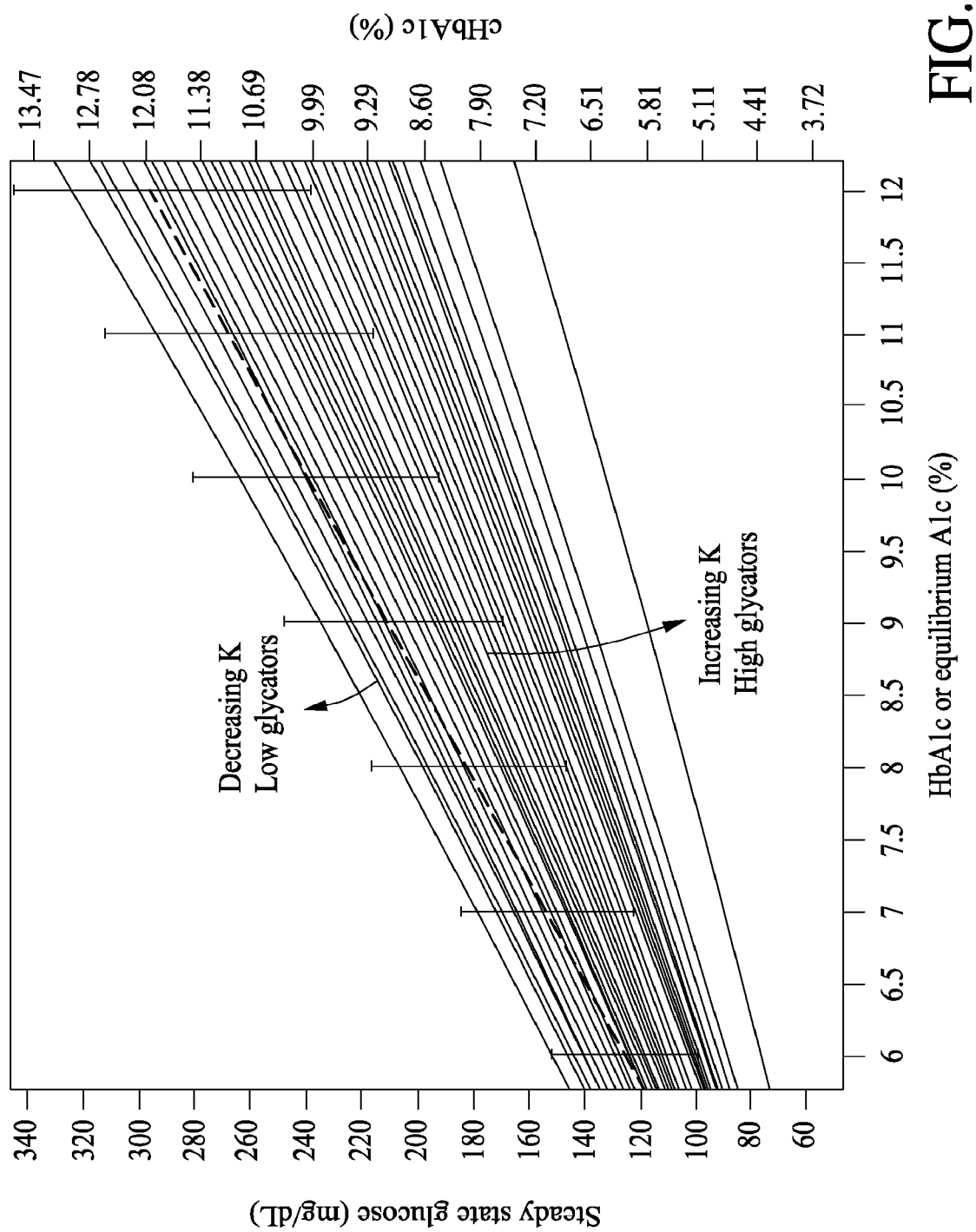
FIG. 11 illustrates the relationship between steady glucose and equilibrium HbA1c (1) as determined using the standard conversion of HbA1c to estimated average glucose (dashed line with error bars) and (2) as measured for the 90 participants (solid lines).

FIG. 11 illustrates the relationship between steady glucose and equilibrium HbA1c (1) as determined using the standard conversion of HbA1c to estimated average glucose (dashed line with error bars) and (2) as measured for the 90 participants (solid lines). These individual curves (solid lines) represent the agreement of average glucose with laboratory measure HbA1c under the condition of their average glucose level being stable for days-to-weeks. The model suggests that the relationship of glucose-to-HbA1c is not constant, with larger changes in glucose needed to achieve the same change in HbA1c as levels of the latter marker increase. Contrary to prior assessments of the glycation index, the kinetic model of the present disclosure suggests that an individual's glycation index will not be constant across all levels of HbA1c. Unlike eHbA1c, a key advantage of cHbA1c is its ability to account for individual variation in glycation. Individuals with lower K are "low glycators", and have higher average glucose levels for a given HbA1c level, with the reverse being true for those with high K values.

Figure 12:
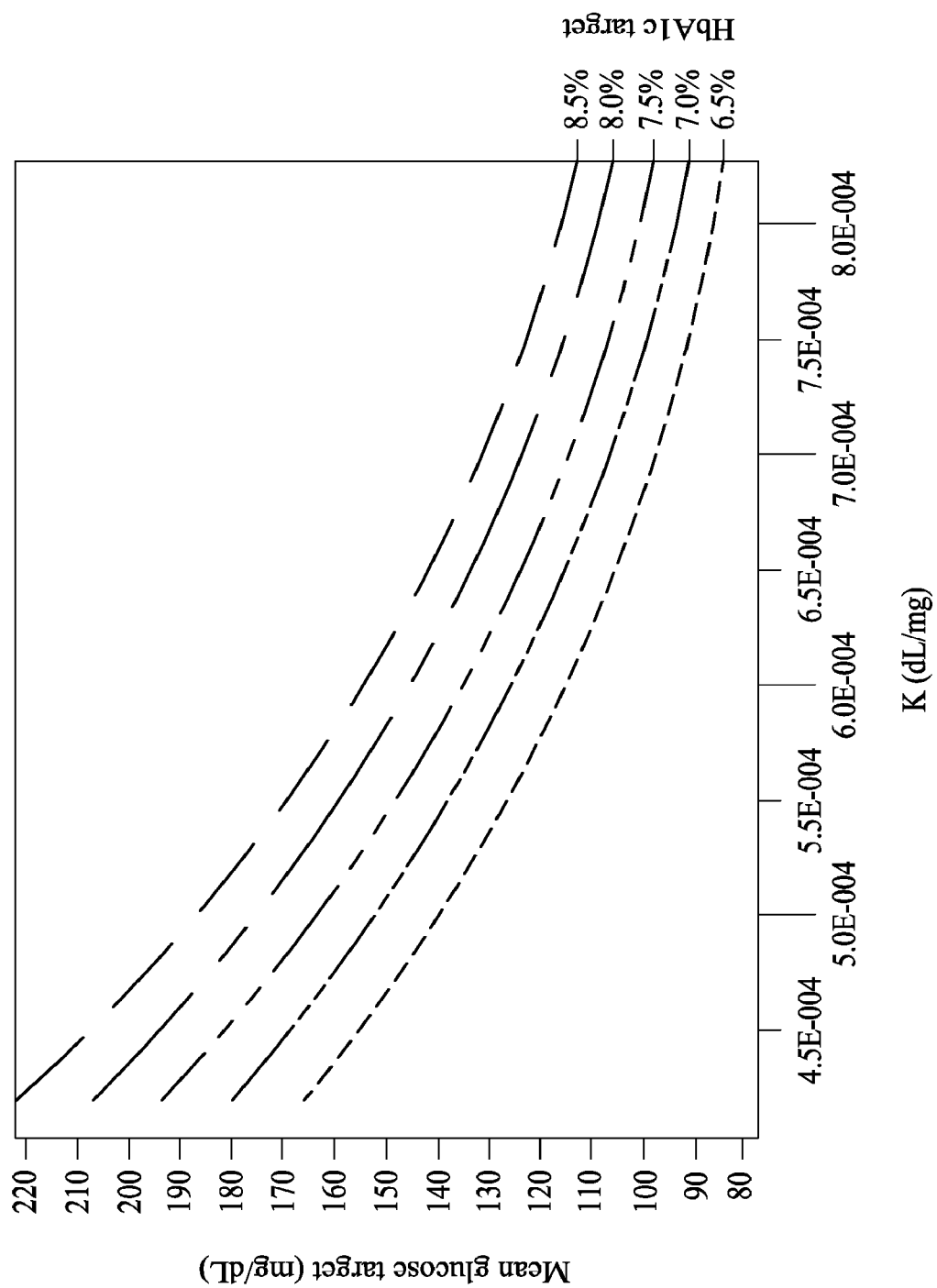
FIG. 12 illustrates the relationship between K (dL/mg) and mean glucose level target (mg/dl) for varying HbA1c target values using the kinetic model of the present disclosure.

Using the kinetic model of the present disclosure, a relationship between K (dL/mg) and mean glucose level target (mg/dL) is illustrated in FIG. 12 plotted for varying HbA1c target values. That is, if a subject is targeting a specific HbA1c value (e.g., for a subsequent HbA1c measurement or cHbA1c estimation) and has a known K value (e.g., based on a plurality of measured glucose levels and at least one measured HbA1c), a mean glucose target can be derived and/or identified for the subject over the time period in which the subject is targeting the HbA1c value.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The invention claimed is:

1. A system for determining at least one glucose level target comprising:
an analyte sensor configured to measure a glucose level in a bodily fluid of a subject; and
a monitoring device comprising:
one or more processors; and
a memory operatively coupled to the one or more processors storing instructions which, when executed by the one or more processors, causes the one or more processors to:
receive a first plurality of glucose levels in the bodily fluid over a first plurality of time periods $(t_i=t_1 \ldots t_z)$ from the analyte sensor, where i=1 for a first time period of the plurality of time periods and i=z for a last time period of the plurality of time periods;
receive a first glycated hemoglobin (HbA1c) level for the subject corresponding to an end of the last time period of the first plurality of time periods;
determine, based on (1) the first plurality of glucose levels and (2) the first HbA1c level, a red blood cell glycation rate constant $k_{gly}$ using Equation A:

$$EA=[G]/((k_{age}/k_{gly})+[G]) \quad \text{Equation A}$$

where EA is the first HbA1c, [G] is an average glucose level over the first plurality of time periods based on the first plurality of glucose levels, and $k_{age}$ is a constant, estimated, or calculated red blood cell elimination constant;
adjust at least one glucose level target based on the determined red blood cell glycation rate constant $(k_{gly})$, wherein the at least one glucose level target is a personalized lower glucose limit (GL) based on Equation B:

$$GL=(LGL*k_{gly}^{ref})/k_{gly}^{sub} \quad \text{Equation B}$$

where $k_{gly}^{ref}$ is a red blood cell location constant $(k_{gly})$ for a normal person, $k_{gly}^{sub}$ is the determined red blood cell gylcation rate constant $(k_{gly})$, and where LGL is an accepted normal lower glucose limit; and
a delivery system configured to receive the at least one glucose level target and treat the subject based on the at least one glucose level target, wherein treating the subject comprises administering and/or adjusting based on the at least one glucose level target: an insulin dosage, a glycation-medication dosage, or a combination thereof.

2. The system of claim 1, wherein the personalized lower glucose limit equals $3.35 \times 10-4/k_{gly} \pm 7\%$.

3. The system of claim 1, further comprising: a display, wherein the instructions which, when executed by the one or more processors, causes the one or more processors to further: display the at least one glucose level target on the display.

4. The system of claim 3, wherein the instructions which, when executed by the one or more processors, causes the one or more processors to further:
receive a second plurality of glucose levels in the bodily fluid over a second plurality of time periods after the first plurality of time periods from the analyte sensor; and
display an alarm on the display based on a determination that a glucose level from the second plurality of glucose levels is outside the at least one glucose level target.

5. The system of claim 1, wherein the instructions, when executed, cause the one or more processors to:
determine the insulin dosage based on the at least one glucose level target; and
transmit the insulin dosage to an insulin pump.

6. A method for determining at least one glucose level target comprising:
receiving a first plurality of glucose levels for a subject over a first plurality of time periods $(t_i=t_1 \ldots t_z)$, where i=1 for a first time period of the plurality of time periods and i=z for a last time period of the plurality of time periods;

receiving a first glycated hemoglobin (HbA1c) level for the subject corresponding to an end of the last time period of the first plurality of time periods;

determining, based on (1) the first plurality of glucose levels and (2) the first HbA1c level, a red blood cell glycation rate constant ($k_{gly}$) using Equation A:

$$EA = [G]/\left(\left(\frac{k_{age}}{k_{gly}}\right) + [G]\right) \quad \text{Equation A}$$

where EA is the first HbA1c, [G] is an average glucose level over the first plurality of time periods based on the first plurality of glucose levels, and $k_{age}$ is a constant, estimated, or calculated red blood cell elimination constant; and adjusting at least one glucose level target based on the determined red blood cell glycation rate constant ($k_{gly}$), wherein the at least one glucose level target is a personalized lower glucose limit (GL) based on Equation B:

$$GL = (LGL * k_{gly}^{ref})/k_{gly}^{sub} \quad \text{Equation B}$$

where $k_{gly}^{ref}$ is a red blood cell glycation rate constant ($k_{gly}$) for a normal person, $k_{gly}^{sub}$ is the determined red blood cell glycation constant ($k_{gly}$), and where LGL is an accepted normal lower glucose limit; and treating the subject based on the at least one glucose level target, wherein treating the subject comprises administering and/or adjusting based on the at least one glucose level target: an insulin dosage, a glycation-medication dosage, an exercise regime, a meal intake, or a combination thereof.

7. The method of claim 6, wherein the personalized lower glucose limit equals $3.35 \times 10-4/k_{gly} \pm 7\%$.

8. The method of claim 6, wherein the first plurality of glucose levels are measured in a bodily fluid selected from the group consisting of: blood, dermal fluid, interstitial fluid, or a combination thereof.

9. The method of claim 6 further comprising: displaying the at least one glucose level target.

10. The method of claim 6 further comprising:
receiving a glucose level of the subject after adjusting the at least one glucose level target; and
displaying an alarm based on a determination that the glucose level of the subject after adjusting the at least one glucose level target is outside the at least one glucose level target.

11. A system for determining at least one glucose level target comprising:
an analyte sensor configured to measure a glucose level in a bodily fluid of a subject;
a monitoring device comprising:
one or more processors; and
a memory operatively coupled to the one or more processors storing instructions which, when executed by the one or more processors, causes the one or more processors to:
receive a first plurality of glucose levels in the bodily fluid over a first plurality of time periods ($t_i = t_1 \ldots t_z$) from the analyte sensor, where i=1 for a first time period of the plurality of time periods and i=z for a last time period of the plurality of time periods;
receive a first glycated hemoglobin (HbA1c) level for the subject corresponding to an end of a last time period of the first plurality of time periods;

determine, based on (1) the first plurality of glucose levels and (2) the first HbA1c level, an apparent glycation constant (K) using Equation A:

$$HbA1c_z = \left(\frac{(K*k_{age})[G_z]}{k_{age} + (K*k_{age})[G_z]}\right)\left(1 - e^{-((K*k_{age})[G_z] + k_{age})t_z}\right) + \quad \text{Equation A}$$
$$\sum_{i=1}^{z-1}\left[\left(\frac{(K*k_{age})[G_i]}{k_{age} + (K*k_{age})[G_i]}\right)\right.$$
$$\left.\left(1 - e^{-((K*k_{age})[G_i] + k_{age})t_i}\right)\prod_{j=i+1}^{z} e^{-((K*k_{age})[G_j] + k_{age})t_j}\right]$$

where $k_{age}$ is a red blood cell elimination constant and is an estimated value in Equation A, HbA1c, is the first HbA1c level, where $[G_z]$ is an average glucose level over the last time period of the first plurality of time periods, where $[G_i]$ is an average glucose level over a corresponding time period of the first plurality of time periods, where $[G_j]$ is an average glucose level over a corresponding time period of the first plurality of time periods, where $t_i$ is a length of time interval of each time period in the first plurality of time periods;

adjust at least one glucose level target based on the determined apparent glycation constant (K), wherein the at least one glucose level target is selected from the group consisting of a personalized lower glucose limit (GU) based on Equation B and a personalized target glucose average (GT) based on Equation C:

$$GU = AU/(K(1-AU)) \quad \text{Equation B}$$

where AU is an accepted normal HbA1c upper limit, $$GT = AT/(K(1-AT)) \quad \text{Equation C}$$

where AT is a target HbA1c level; and
a delivery system configured to receive the at least one glucose level target and treat the subject based on the at least one glucose level target, wherein treating the subject comprises administering and/or adjusting based on the at least one glucose level target: an insulin dosage, a glycation-medication dosage, or a combination thereof.

12. The system of claim 11, wherein the personalized upper glucose limit equals $0.087/K \pm 7\%$.

13. The system of claim 11 further comprising:
a display, wherein the instructions which, when executed by the one or more processors, causes the one or more processors to further: display the at least one glucose level target on the display.

14. The system of claim 13, wherein the instructions which, when executed by the one or more processors, causes the one or more processors to further:
receive a second plurality of glucose levels in the bodily fluid over a second plurality of time periods after the first plurality of time periods from the analyte sensor; and
display an alarm based on a determination that a glucose level from the second plurality of glucose levels is outside the at least one glucose level target on the display.

15. The system of claim 11, wherein the instructions, when executed, cause the one or more processors to: determine the insulin dosage based on the at least one glucose level target;
and transmit the insulin dosage to an insulin pump.

16. A method for determining at least one glucose level target comprising:

receiving a first plurality of glucose levels for a subject over a first plurality of time periods ($t_i = t_1 \ldots t_z$), where i=1 for a first time period of the plurality of time periods and i=z for a last time period of the plurality of time periods;

receiving a first glycated hemoglobin (HbA1c) level for the subject corresponding to an end of the last time period of the first plurality of time periods;

determining, based on (1) the first plurality of glucose levels and (2) the first HbA1c level, a red blood cell glycation rate constant ($k_{gly}$) using Equation A:

$$HbA1c_z = \left(\frac{(K*k_{age})[G_z]}{k_{age} + (K*k_{age})[G_z]}\right)\left(1 - e^{-((K*k_{age})[G_z]+k_{age})t_z}\right) +$$
$$\sum_{i=1}^{z-1}\left[\left(\frac{(K*k_{age})[G_i]}{k_{age} + (K*k_{age})[G_i]}\right)\right.$$
$$\left.\left(1 - e^{-((K*k_{age})[G_i]+k_{age})t_i}\right)\sum_{j=i+1}^{z} e^{-((K*k_{age})[G_j]+k_{age})t_j}\right]$$

Equation A where $k_{age}$ is a red blood cell elimination constant and is an estimated value in Equation A, HbA1c, is the first HbA1c level, where [$G_z$] is an average glucose level over the last time period of the first plurality of time periods, where [$G_i$] is an average glucose level over a corresponding time period of the first plurality of time periods, where [$G_j$] is an average glucose level over a corresponding time period of the first plurality of time periods, where $t_i$ is a length of time interval of each time period in the first plurality of time periods;

adjusting at least one glucose level target based on the determined apparent glycation constant (K), wherein the at least one glucose level target is selected from the group consisting of a personalized upper glucose limit (GU) based on Equation B and a personalized-target glucose average (GT) based on Equation C:

GU=AU/(*K*(1−AU))        Equation B where AU is an accepted normal HbA1c upper limit, GT=AT/(*K*(1−AT))        Equation C where AT is a target HbA1c level; and treating the subject based on the at least one glucose level target, wherein treating the subject comprises administering and/or adjusting based on the at least one glucose level target:

an insulin dosage, a glycation-medication dosage, or a combination thereof.

17. The method of claim 16, wherein the personalized upper glucose limit equals 0.087/K±7%.

18. The method of claim 16, wherein the first plurality of glucose levels are measured in a bodily fluid selected from the group consisting of: blood, dermal fluid, interstitial fluid, or a combination thereof.

19. The method of claim 16 further comprising: displaying the at least one glucose level target.

20. The method of claim 16 further comprising: receiving a glucose level of the subject after adjusting the at least one glucose level target; and displaying an alarm based on a determination that the glucose level of the subject after adjusting the at least one glucose level target is outside the at least one glucose level target.

* * * * *